(12) United States Patent
Goldfarb et al.

(10) Patent No.: US 7,976,559 B2
(45) Date of Patent: Jul. 12, 2011

(54) ARTICULATED SURGICAL PROBE AND METHOD FOR USE

(75) Inventors: Michael A. Goldfarb, Little Silver, NJ (US); Eric Goldfarb, San Francisco, CA (US)

(73) Assignee: Dynamic Surgical Inventions, LLC, Little Silver, NJ (US)

( * ) Notice: Subject to any disclaimer, the term of this patent is extended or adjusted under 35 U.S.C. 154(b) by 0 days.

(21) Appl. No.: 11/263,744

(22) Filed: Nov. 1, 2005

(65) Prior Publication Data

US 2006/0094932 A1    May 4, 2006

Related U.S. Application Data

(60) Provisional application No. 60/625,153, filed on Nov. 4, 2004.

(51) Int. Cl.
*A61B 17/00* (2006.01)
*A61B 1/00* (2006.01)

(52) U.S. Cl. ........................................ 606/190; 600/141

(58) Field of Classification Search .................. 606/170, 606/190, 105, 205, 130, 49–50; 600/139, 600/141, 142, 146, 149, 229; 604/528, 95.04; 434/262, 266, 267
See application file for complete search history.

(56) References Cited

U.S. PATENT DOCUMENTS

| 422,373 | A | | 3/1890 | Caldwell |
| 3,144,020 | A | | 8/1964 | Zingale et al. |
| 4,259,955 | A | * | 4/1981 | Ritter ................................. 604/1 |
| 5,358,478 | A | * | 10/1994 | Thompson et al. ......... 604/95.04 |
| 5,405,344 | A | | 4/1995 | Williamson et al. |
| 5,441,494 | A | | 8/1995 | Ortiz |
| 5,454,827 | A | * | 10/1995 | Aust et al. ...................... 606/170 |
| 5,522,788 | A | * | 6/1996 | Kuzmak ........................ 600/141 |
| 5,549,636 | A | * | 8/1996 | Li ................................... 606/206 |
| 5,599,151 | A | * | 2/1997 | Daum et al. ...................... 414/7 |
| 5,704,898 | A | | 1/1998 | Kokish |
| 5,807,376 | A | | 9/1998 | Viola et al. |
| 5,810,716 | A | | 9/1998 | Mukherjee et al. |
| 5,813,813 | A | | 9/1998 | Daum et al. |
| 6,200,311 | B1 | | 3/2001 | Danek et al. |
| 6,475,135 | B1 | | 11/2002 | Levy |
| 6,487,439 | B1 | | 11/2002 | Skladnev et al. |
| RE38,335 | E | | 11/2003 | Aust et al. |
| 6,913,627 | B2 | | 7/2005 | Matsuda |
| 7,090,637 | B2 | | 8/2006 | Danitz et al. |
| 2003/0236493 | A1 | * | 12/2003 | Mauch ....................... 604/95.04 |
| 2006/0094933 | A1 | | 5/2006 | Goldfarb et al. |

* cited by examiner

*Primary Examiner* — Darwin P Erezo
*Assistant Examiner* — Melissa Ryckman
(74) *Attorney, Agent, or Firm* — Levine Bagade Han LLP

(57) ABSTRACT

A surgical probe includes an articulated digit located at a distal end of a positioning shaft having a longitudinal axis. An actuator is located at a proximal end of the positioning shaft that is operatively connected to the articulated digit so as to move it between a continuous range of positions from an extended position to a substantially curved position while maintaining a kinesthetic relationship between a surgeon's finger engaging the actuator and the articulated digit. Preferably, the surgeons finger position and shape directly correspond to the position and shape of the articulated digit. A method is provided for probing, dissecting, and retracting anatomical structures.

46 Claims, 23 Drawing Sheets

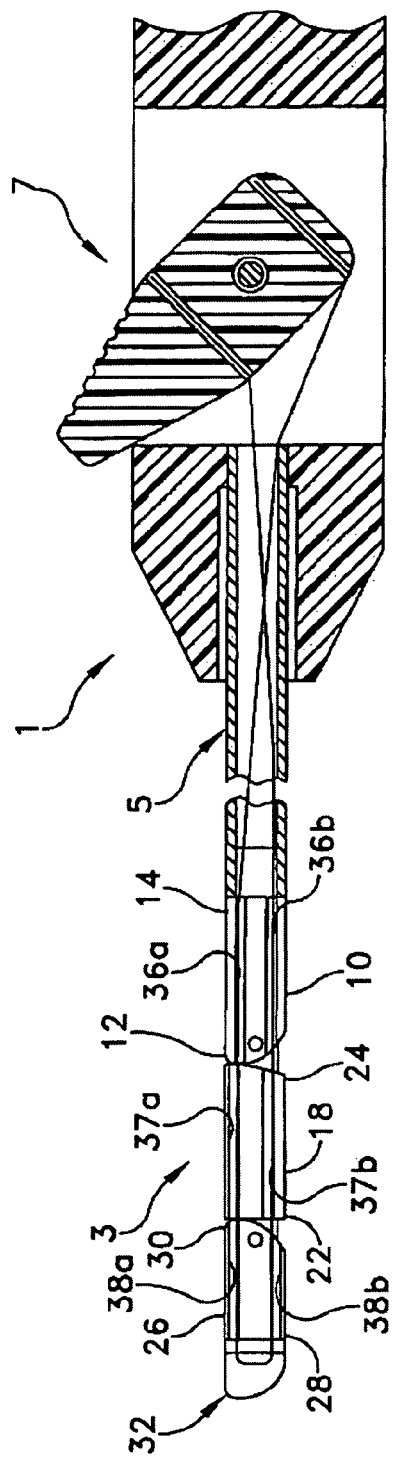
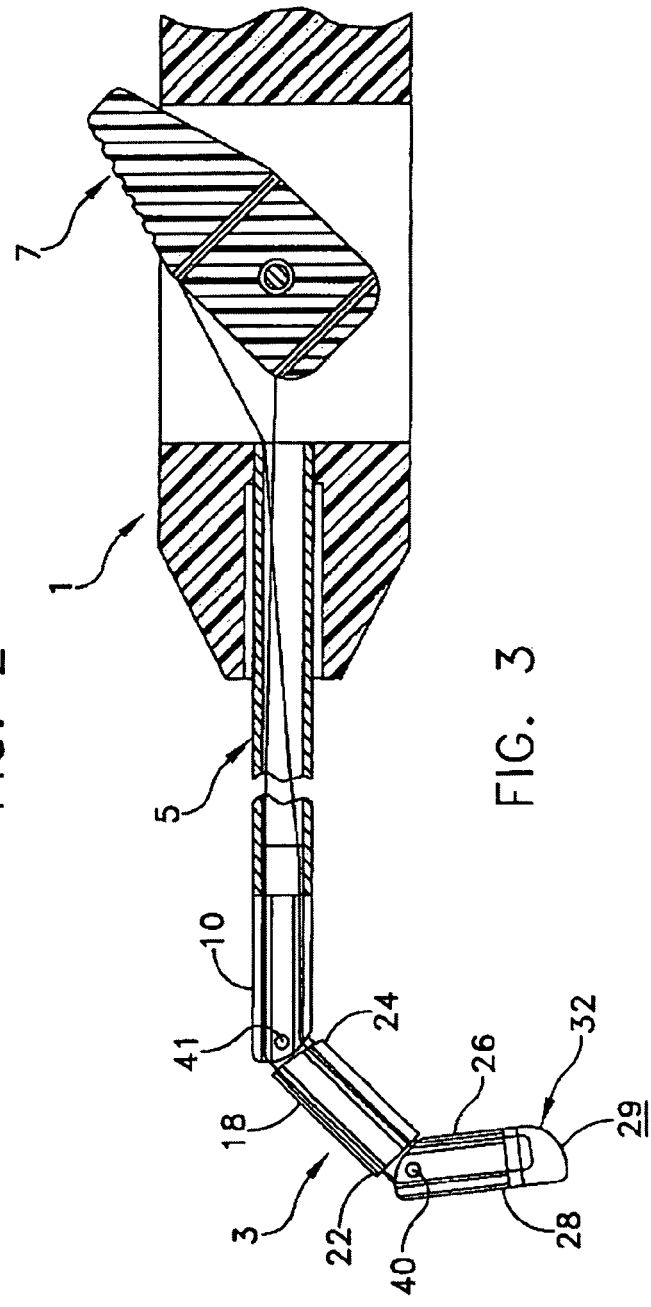
FIG. 2
FIG. 3

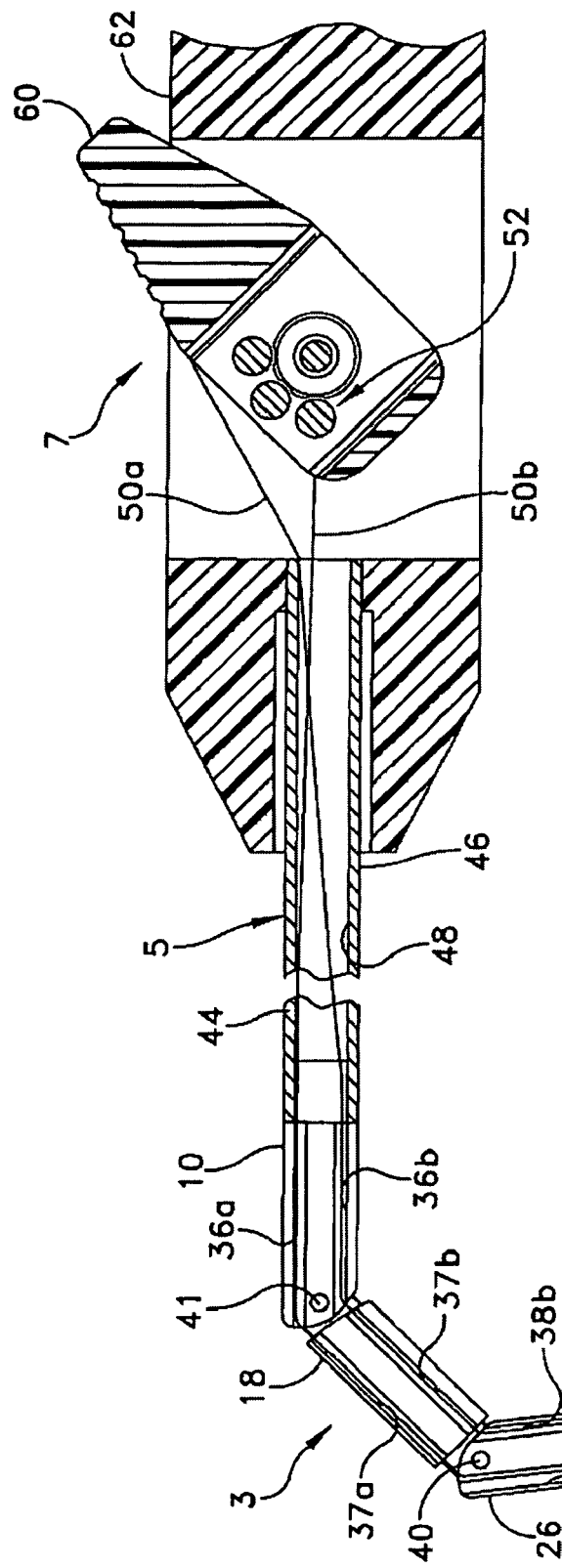
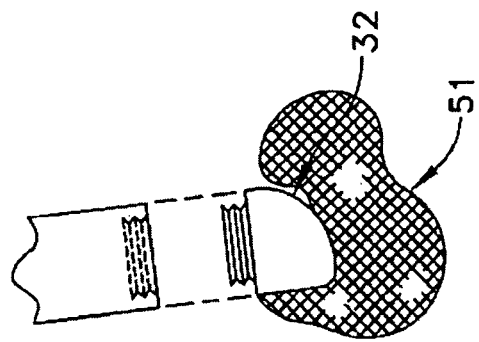
FIG. 5
FIG. 5A

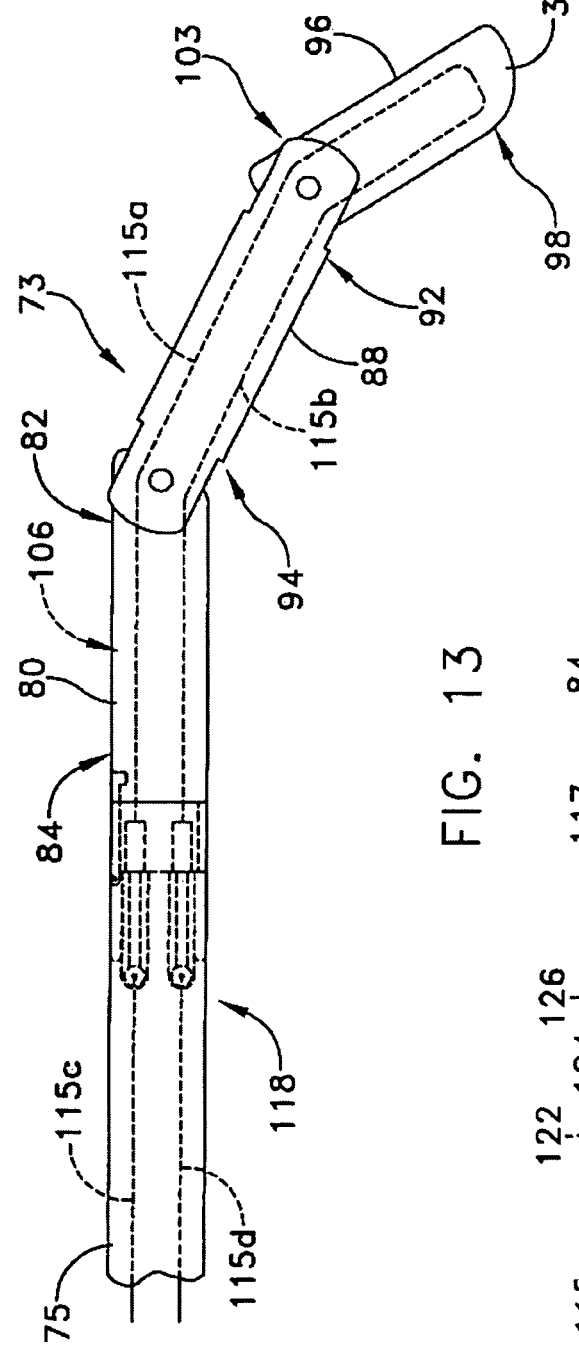
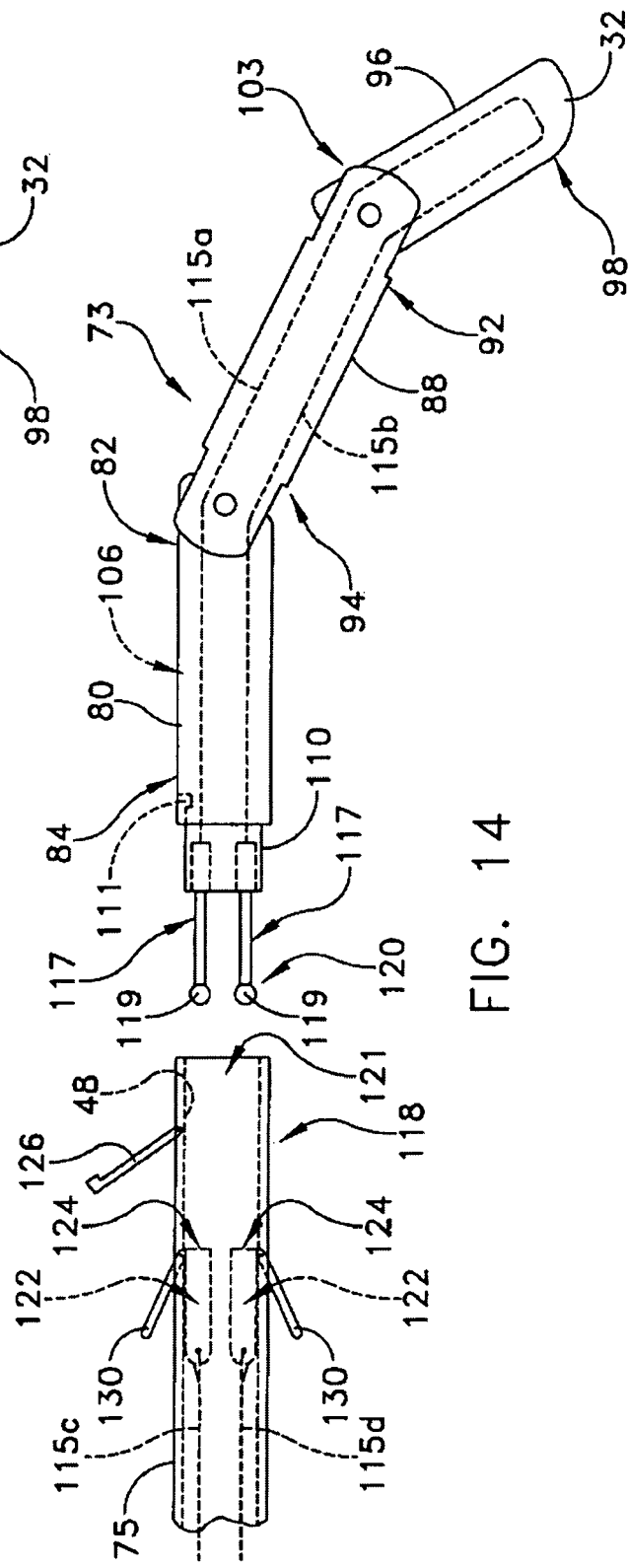
FIG. 13
FIG. 14

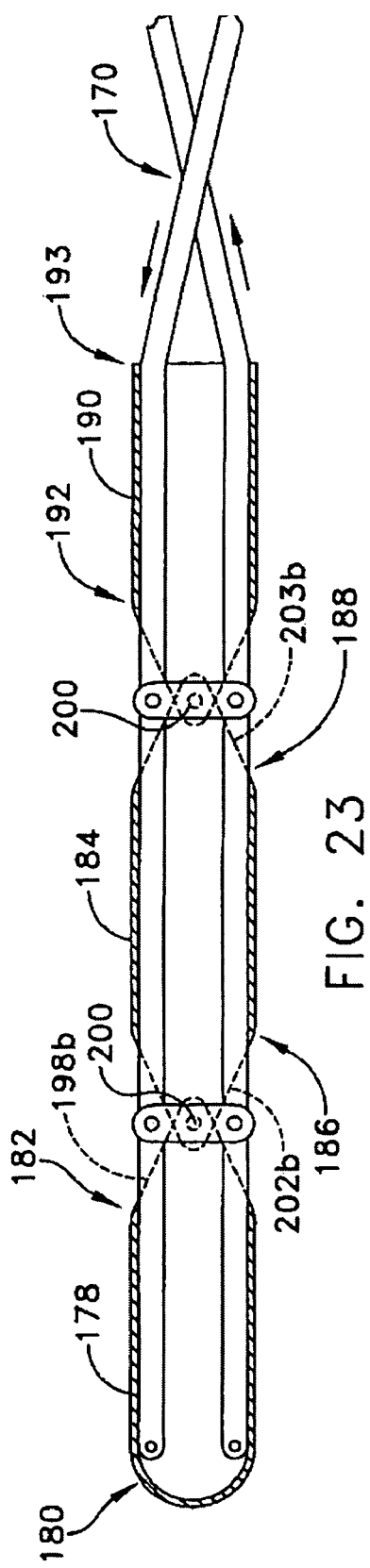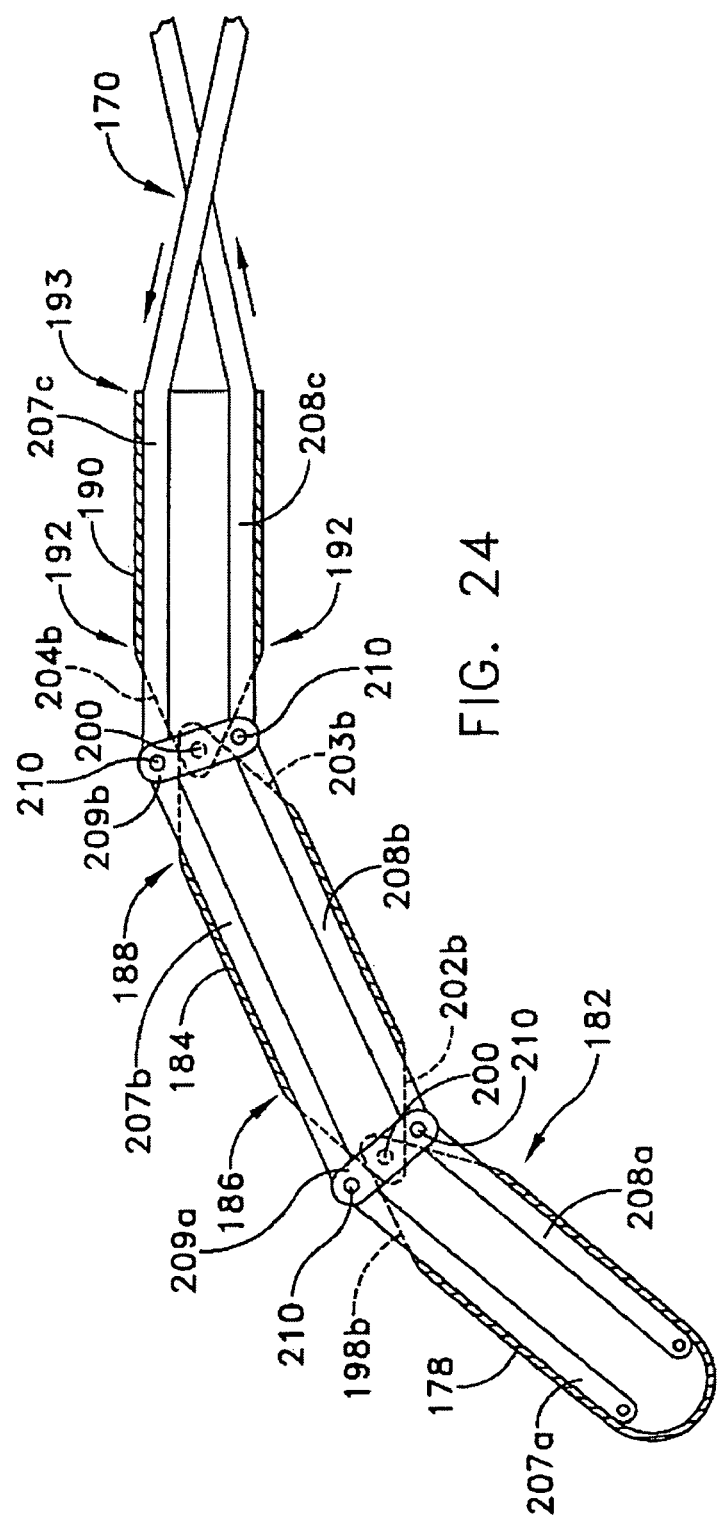

ARTICULATED SURGICAL PROBE AND METHOD FOR USE

This nonprovisional patent application claims priority from provisional patent application Ser. No. 60/625,153, filed Nov. 4, 2004, entitled Laparoscopic Finger, which provisional application is incorporated herein by reference in its entirety.

FIELD OF THE INVENTION

The present invention relates to surgical devices, and more particularly to an articulated finger-like probe adapted for positioning within a patient's body, and suitable for assisting minimally-invasive surgery. The present invention further relates to surgical procedures in which one or more articulated finger-like probes of the present invention are used to assist minimally-invasive surgical procedures.

BACKGROUND OF THE INVENTION

There has been a discernible tendency in surgery to develop procedures and devices that reduce the need for major surgical incisions which entails extended hospitalization, and increased wound complications such as infections and post operative hernias. These minimally-invasive surgical procedures and devices (i.e., endoscopic and/or laparoscopic surgical procedures and devices) have been especially, but not exclusively, important in abdominal, thoracic, gynecologic, urologic and orthopedic operations. Typically, a scope that is arranged with an external camera and light source, enter the abdominal cavity or joint through two or more small incisions along with one or more surgical instruments. The indicated surgical procedure is then performed by manipulating the long-handled surgical instruments while viewing their actions on a video monitor that receives images of the surgical site from the video camera.

While certain minimally invasive surgical techniques are in practice, there are significant disadvantages which have, to date, limited the applications for these techniques. For example, the standard laparoscopic instruments used in many minimally invasive procedures do not provide the surgeon the ability to mimic open surgical hand dissection techniques. Additionally, manipulation of fragile friable tissues can be difficult and often damaging while manipulating sharp and or small tipped tools inside the body cavity from outside the body. It is often the case that the surgeon would ideally prefer, to actually handle, manipulate, or even dissect a portion of tissue with his or her fingers during surgery, as this activity often provides the most sensitive feedback to the surgeon.

Many minimally invasive techniques are difficult due to the limited access provided to the surgical site, in which tools and viewing scopes are often inserted through narrow cannulae. Some surgeons, therefore, adopt a "hand assisted" approach. To accomplish this approach an incision large enough to accommodate a surgeon's hand is made in the abdomen. The surgeon then views his or her hand dissecting, on a video monitor, enabled by a laparoscope positioned appropriately. Unfortunately most of the time the surgeon's dissecting hand blocks the view of the dissection performed by the fingers. In addition only the operating surgeon can appreciate the course of the operation when the dissection is accomplished by palpation and direct vision is not possible. For certain operations, the hand assisted approach is a link along the learning curve to a laparoscopic approach. Again, with a hand assisted approach, an incision large enough to accommodate a surgeon's hand is created. An incision that is capable of accommodating a surgeons hand renders the procedure conventionally invasive, even though the laparoscope and other instruments are inserted through other small abdominal openings.

A number of devices have been proposed in the prior art that attempt to simulate the manipulative capabilities of a surgeon's finger during surgery. For example, in U.S. Pat. No. 5,522,788, issued to Kuzmak, a blunt laparoscopic dissector device is provided which includes an elongate dissector element including a "finger-like" flexible distal end portion. A cylinder or barrel member disposed at one end of a pair of pivotable control arms provides rotatable mounting of the dissector element. A control assembly, including a control rod connected to the other control arm and extending along the length of the dissector element, exerts a force on the dissector element so as to produce the desired curvature of the flexible distal end portion. A locking mechanism maintains the force on the dissector element so as to maintain the desired curvature. Rotation of the dissector element within the cylinder allows for control of the movement of the device's tip while holding the device in a comfortable stationary position. This device has a "pistol" style handle and forceps-style finger grips. There is no kinesthetic relationship between the tip of the index finger and the tip of the instrument, such that the precise movement of the finger tip is not reflected exactly by the instrument tip. Tactile feedback may be attenuated by the use of concatenated driving and driven elements.

In U.S. Pat. No. 5,810,716, issued to Mukherjee et al., a surgical device is provided for use in minimally invasive surgery that is suited for tele-surgery. The surgical device provides dexterity through articulation of a plurality of concatenated segments that transfer angular rotational motion from a driving device located at its base to the distal end. Each segment in the mechanism acts as both a driven element and a driving element whereby each segment is articulated so that the total articulation of the mechanism is the sum of the articulation motions of each segment. Here again the kinesthetic relationship between the surgeon's fingertip and the tip of the instrument is not exactly reproduced. The tactile feedback needed by the surgeon may be obfuscated by the use of concatenated driving and driven elements.

In U.S. Pat. No. RE38,335, reissued to Aust et al., a surgical device is provided for use in minimally invasive surgery that includes a handle, a first stem section having a longitudinal axis and extending from the handle, and a tissue engaging member for engaging tissue. A second stem section, connected between the first stem section and the tissue engaging member, has a portion which is bendable and supports the tissue engaging member for movement between a plurality of orientations relative to the axis and to the first stem section. The surgical instrument includes a system for bending the bendable portion of the second stem section to change the orientation of the tissue engaging member relative to the axis and to the first stem section from a first orientation to a second orientation. The bendable portion of the second stem section includes a member for enabling bending movement of the bendable portion to locate the tissue engaging member at the same angle relative to the longitudinal axis of the first stem section at more than one location along the length of the bendable portion. However the exact kinesthetic relationship between the surgeon's fingertip and the instrument tip is not possible. Once again the tactile feedback may be filtered by the handle articulation mechanisms.

The foregoing and other prior art devices do not allow a precise kinesthetic relationship between a surgeon's fingertip and the dissecting instrument tip. Those prior art devices may have a limited tactile sensing ability transferred to the surgeon. PCT/US97/11494 teaches a number of surgical instruments which can be mounted directly on a surgeon's fingertip in a way that the surgeon can insert his or her hand into a natural cavity of the patient or through one or more minimal incisions to perform surgical procedures, and also to use his or her fingers to manipulate tissues, thus enabling the surgeon to perform the procedures with the benefits of minimally invasive surgery, but with much greater tactile sense, control, and ease of manipulation. However, these surgical instruments (i) are carried by a finger and operated by the thumb, and are not applicable for procedures in which a single finger is employed for tactile sensing of an intrabody location; (ii) include an operating head which permanently extends far beyond the fingertip on which the surgical instrument is mounted, which limits the tactile sensing for the surgeon; and/or (iii) prevent tactile sensing by the instrument carrying the fingertip altogether.

There is a widely recognized need for, and it would be highly advantageous to have, a finger-like surgical probe devoid of the limitations associated with prior art instruments, and which closely simulates a surgeon's finger, or fingers, so as to enable a surgeon to handle, manipulate, or dissect a portion of tissue through an incision of the type employed during minimally invasive surgical procedures, and maintain a kinesthetic relationship with the surgeon's fingertip.

SUMMARY OF THE INVENTION

The present invention provides a surgical probe having an articulated digit located at a distal end of a positioning shaft that defines a longitudinal axis. An actuator is located at a proximal end of the positioning shaft and is operatively connected to the articulated digit so as to move the articulated digit between a continuous range of positions from an extended position to a substantially curved position while maintaining a kinesthetic relationship between a surgeon's finger engaging the actuator and the articulated digit, i.e., the extent of flexion or extension of the surgeon's finger is mimicked by the flexion or extension of the articulated digit such that forces transmitted between the surgeon's finger and the articulated digit are transmitted in a manner that provides functional sensation to the operator.

In one embodiment, a surgical probe is provided that includes an articulated digit located at a distal end of a positioning shaft having a longitudinal axis. An actuator is located at a proximal end of the positioning shaft so as to be operatively connected to the articulated digit. In this way, when the actuator moves, a kinesthetic relationship is maintained between a surgeon's finger engaging the actuator and the articulated digit. The articulated digit moves through a continuous range of positions that directly correspond with a continuous range of surgeon's finger positions attained when engaging the actuator so that the articulated digit moves between a fully extended position and a substantially curved or crook position.

In another embodiment, a surgical probe is provided that includes an articulated digit located at a distal end of a positioning shaft having a longitudinal axis, with a bulbous probe-tip that supports a sponge or gauze wad for use in blunt dissection. An actuator is located at a proximal end of the positioning shaft that is operatively connected to the articulated digit. In this way, the articulated digit may move between a continuous range of positions from an extended position to a substantially curved position while maintaining a kinesthetic relationship between a surgeon's finger engaging the actuator and the articulated digit. Preferably, the surgeon's finger position and shape directly correspond to the position and shape of the articulated digit.

In a surgical method according to the invention, a surgeon is provided with a surgical probe that includes an articulated digit located at a distal end of a positioning shaft having a longitudinal axis. An actuator located at a proximal end of the positioning shaft is operatively connected to the articulated digit so as to move the articulated digit between a continuous range of positions from an extended position to a substantially curved or crook position while maintaining a kinesthetic relationship between the surgeon's finger engaging the actuator and the articulated digit. The surgeon positions the surgical probe adjacent to an anatomical structure to be manipulated or palpated, and moves the actuator with a finger so as to arrange the articulated digit in a configuration that closely corresponds to the configuration of that finger. An anatomical structure may then be engaged and retracted, palpated, dissected, or otherwise probed with the articulated digit in a manner corresponding to manual manipulation and palpation of the anatomical structure during open surgical procedures with either gentle or firm movements of the articulated digit, including the application of torque to the anatomical structure.

BRIEF DESCRIPTION OF THE DRAWINGS

These and other features and advantages of the present invention will be more fully disclosed in, or rendered obvious by, the following detailed description of the preferred embodiment of the invention, which are to be considered together with the accompanying drawings wherein like numbers refer to like parts and further wherein:

FIGS. 2-3 are broken-away cross-sectional views of the articulated surgical probe shown in FIG. 1, illustrating the correspondence between a toggle actuator position and the shape of an articulated digit formed in accordance with the invention;

FIG. 5 is a broken-away cross-sectional view, similar to that of FIG. 4, a "peanut" gauze wad dissection implement wrapped around the entire tip of the articulated digit;

FIG. 5a is a broken-away, enlarged view of an alternative embodiment of the present invention including a detachable peanut dissector tip;

FIG. 13 is a broken-away side elevational view of a fully assembled distal portion of the articulated surgical probe shown in FIG. 12;

FIG. 14 is a broken-away side elevational view of a fully detached distal portion of the articulated surgical probe shown in FIG. 12;

FIGS. 23-24 are broken-away cross-sectional views, partially in phantom of a distal portion of the articulated surgical probe shown in FIG. 22, illustrating an alternative actuation mechanism;

DETAILED DESCRIPTION OF THE PREFERRED EMBODIMENT

Figure 1:
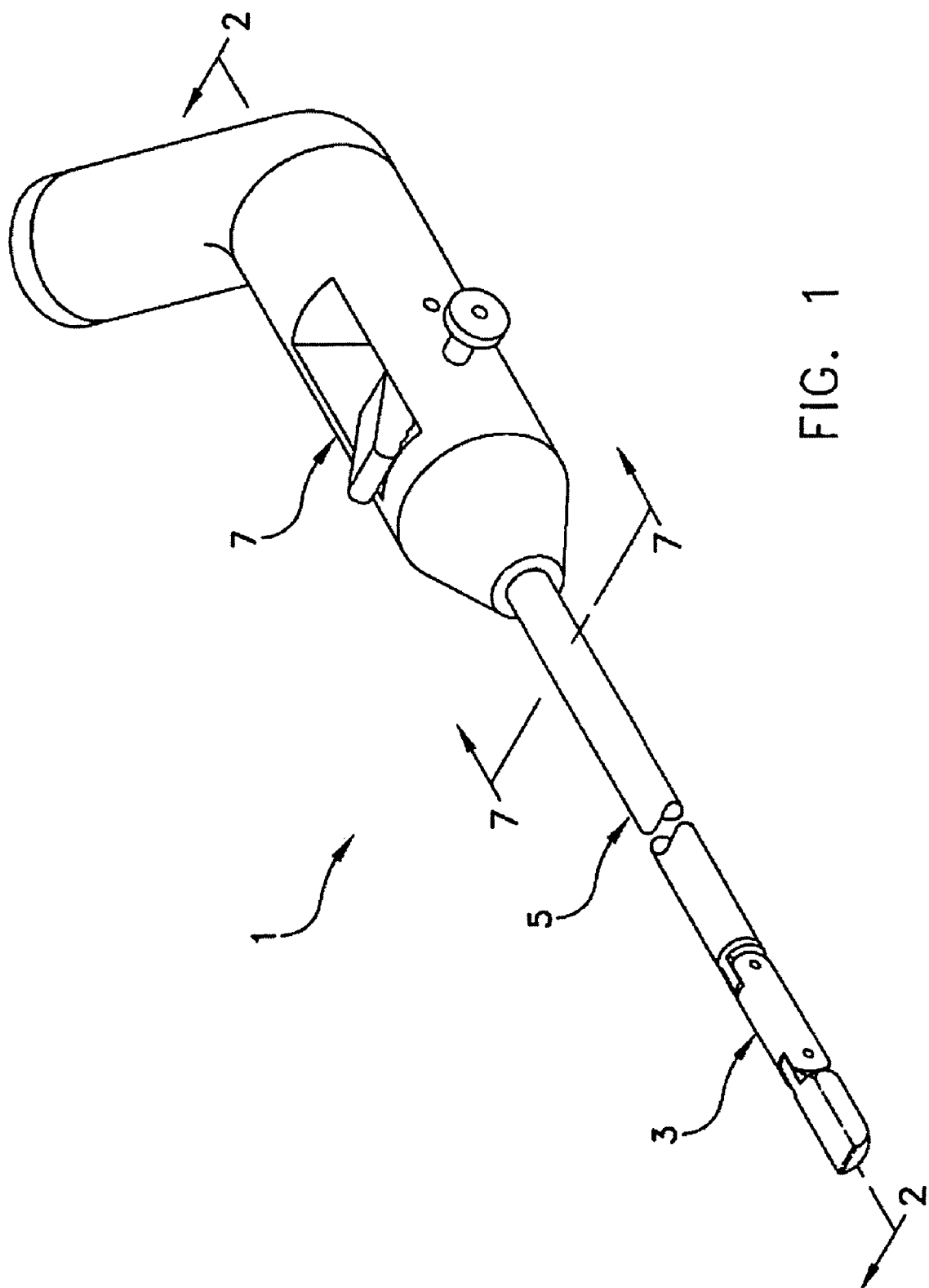
FIG. 1 is a perspective view of an articulated surgical probe formed in accordance with the present invention.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Referring to FIGS. 1-3, an articulated surgical probe 1 formed in accordance with the present invention may be remotely and continuously contracted and extended in concert with a surgeon's finger, for remote manipulation or dissection of soft tissue and the like during minimally invasive surgical procedures, and without substantial loss of kinesthetic feedback or haptic sensation. One preferred embodiment of articulated surgical probe 1 comprises a digit 3, a positioning shaft 5, and an actuator assembly 7. More particularly, digit 3 includes an elongate proximal phalanx 10 having a curved distal end 12 and a proximal end 14, a middle phalanx 18 having a flat distal end 22 and a curved proximal end 24, a distal phalanx 26 having a distal end 28 and a curved proximal end 30, and a bulbous probe-tip 32 (FIGS. 2 and 3). In one embodiment, proximal phalanx 10 also includes a pair of radially spaced-apart, longitudinally oriented through-bores 36a, 36b, middle phalanx 18 includes a pair of radially spaced-apart, longitudinally oriented through-bores 37a, 37b, and distal phalanx 26 includes a pair of radially spaced-apart, longitudinally oriented through-bores 38a, 38b.

When digit 3 is assembled, curved proximal end 30 of distal phalanx 26 is pivotally connected to flat distal end 22 of middle phalanx 18 by, e.g., a pivot pin 40, and curved distal end 12 of elongate proximal phalanx 10 is pivotally connected to curved proximal end 24 of middle phalanx 18 by a pivot pin 41. In this way, the phalanges may pivot relative to one another so that digit 3 comprises a range of motion that is continuous between a first fully extended position that may be, for example, aligned with a longitudinal axis 43 of positioning shaft 5, and often substantially coaxial with positioning shaft 5, and a final substantially curved, flexed, crook, or "hook-shaped" position, i.e., curved or bent relative to positioning shaft 5.

Figure 9:
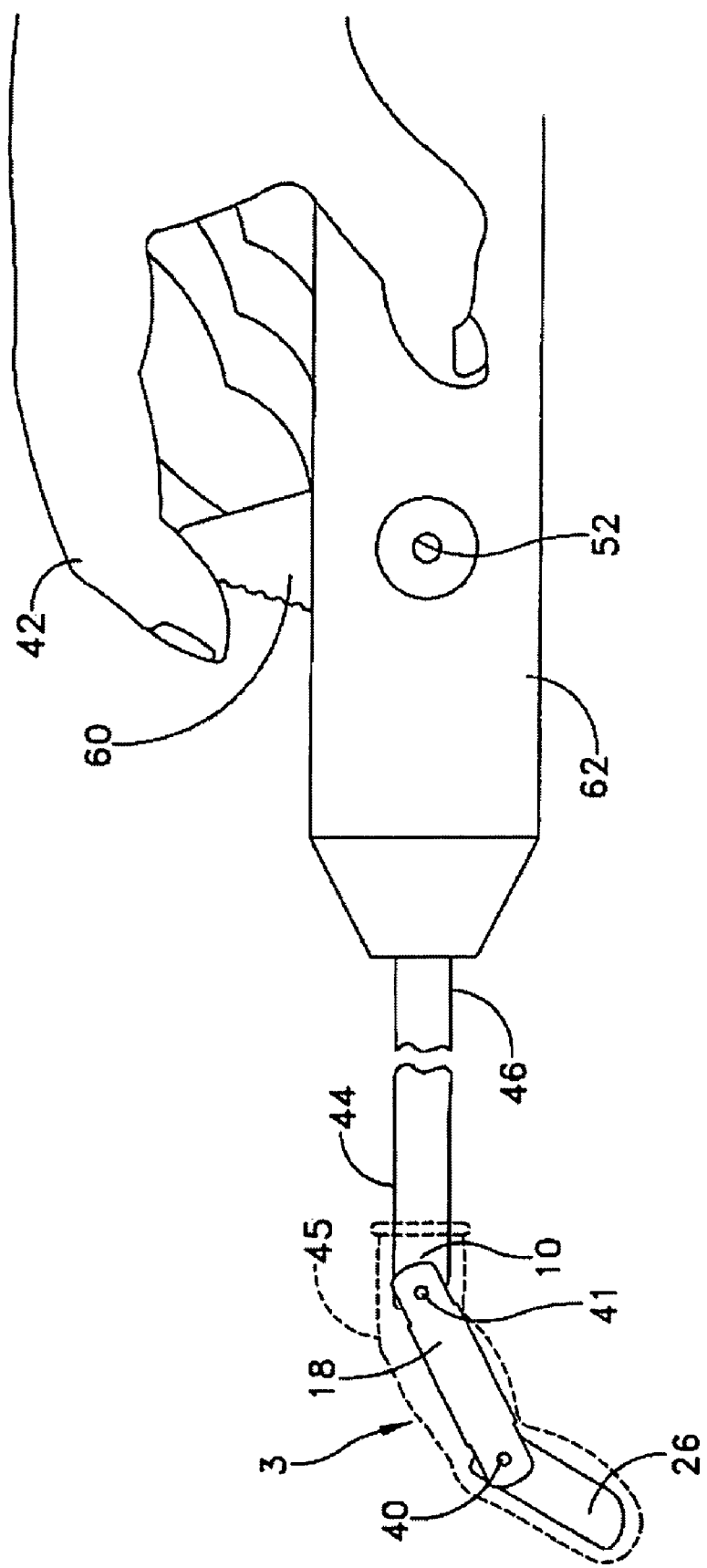
FIG. 9 is a side elevational view, similar to FIG. 8, illustrating another correspondence between a surgeon's finger, the toggle actuator, and a curving position of an articulated digit.
Figure 10:
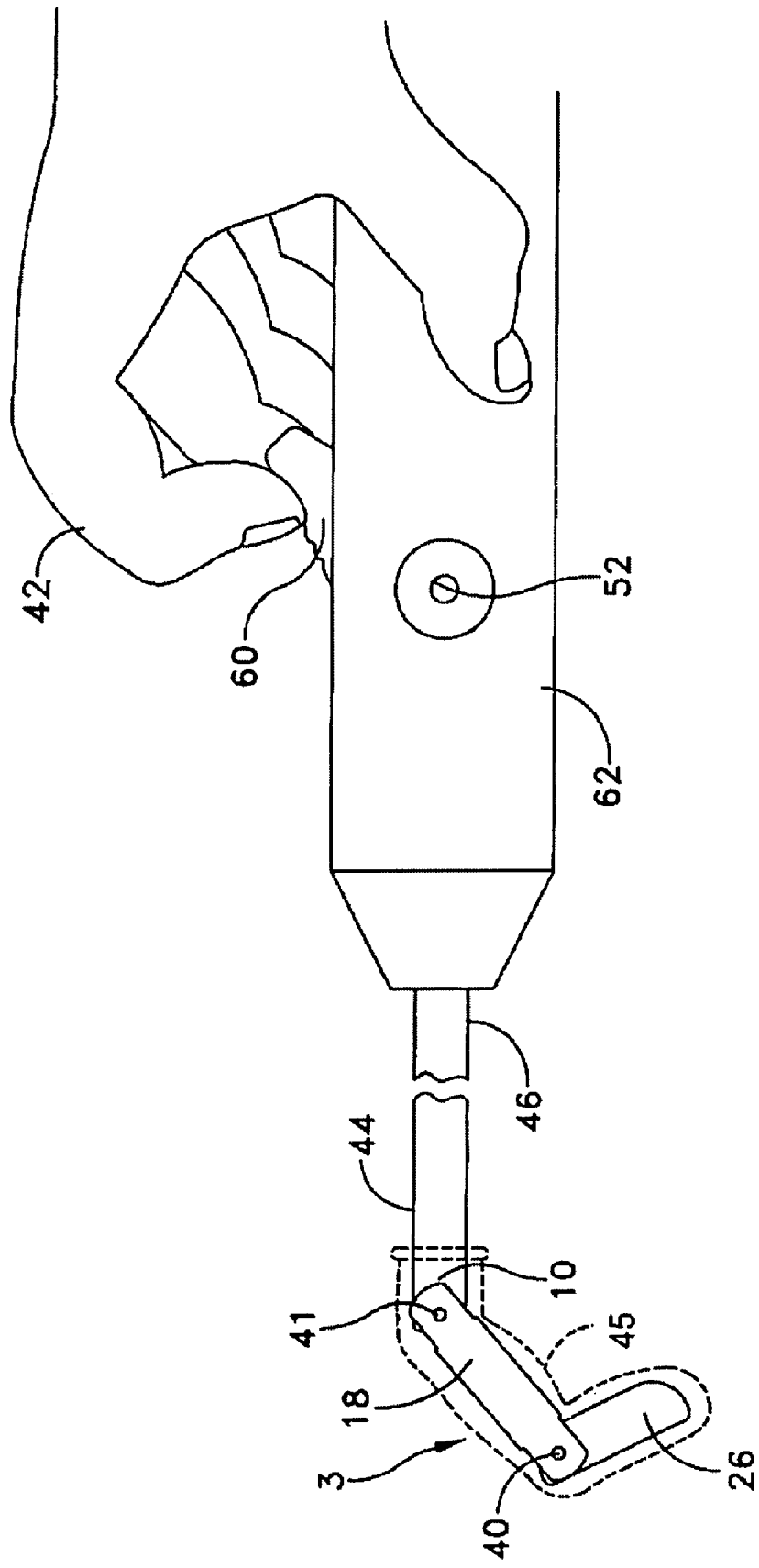
FIG. 10 is a side elevational view, similar to FIGS. 8 and 9, showing yet a further illustration of the correspondence between a surgeon's finger, the toggle actuator, and a crook position of the articulated digit.
Figure 11:
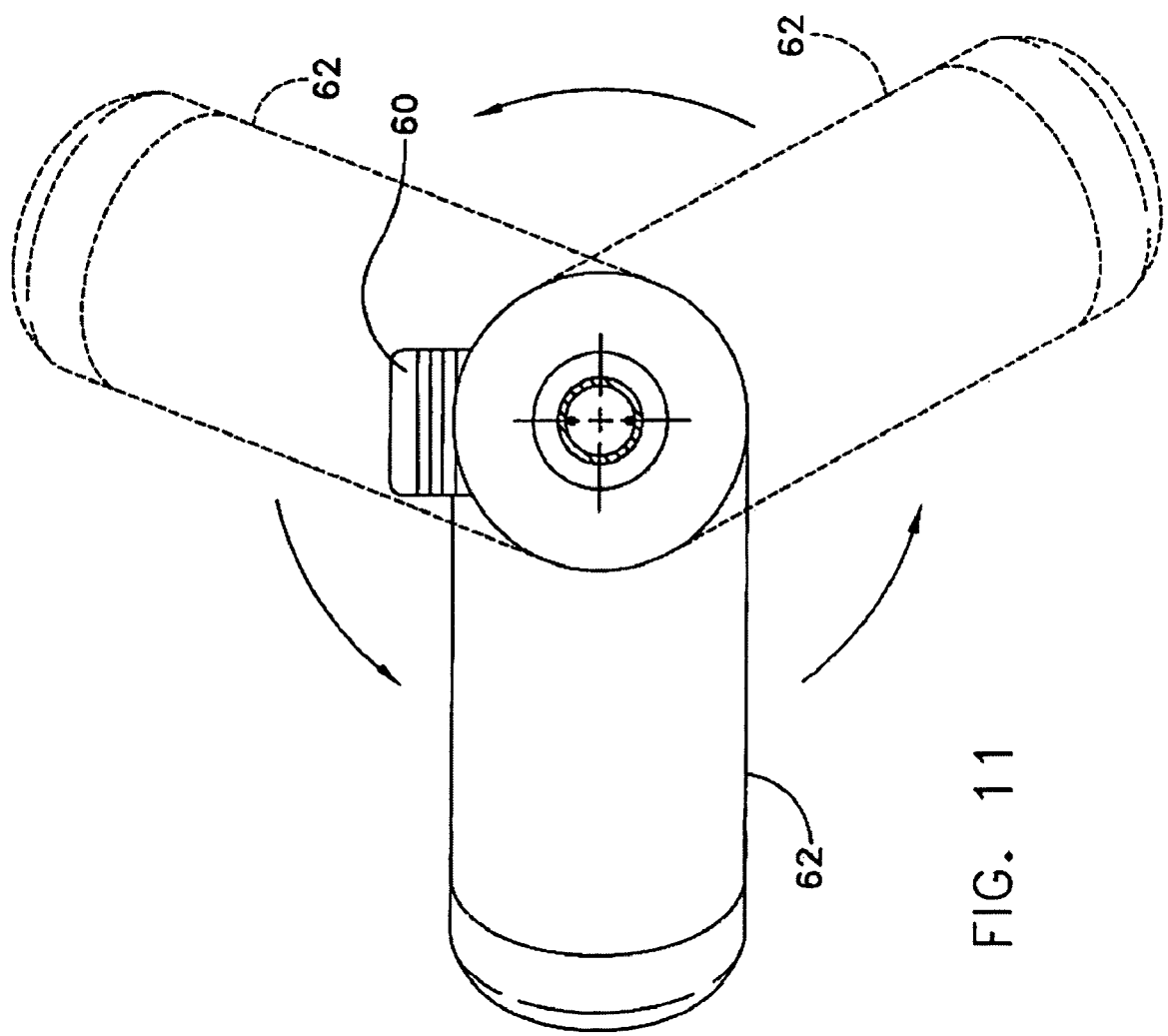
FIG. 11 is an end-on view of an articulated surgical probe illustrating a rotational handle located behind a toggle actuator of the device.
Figure 12:
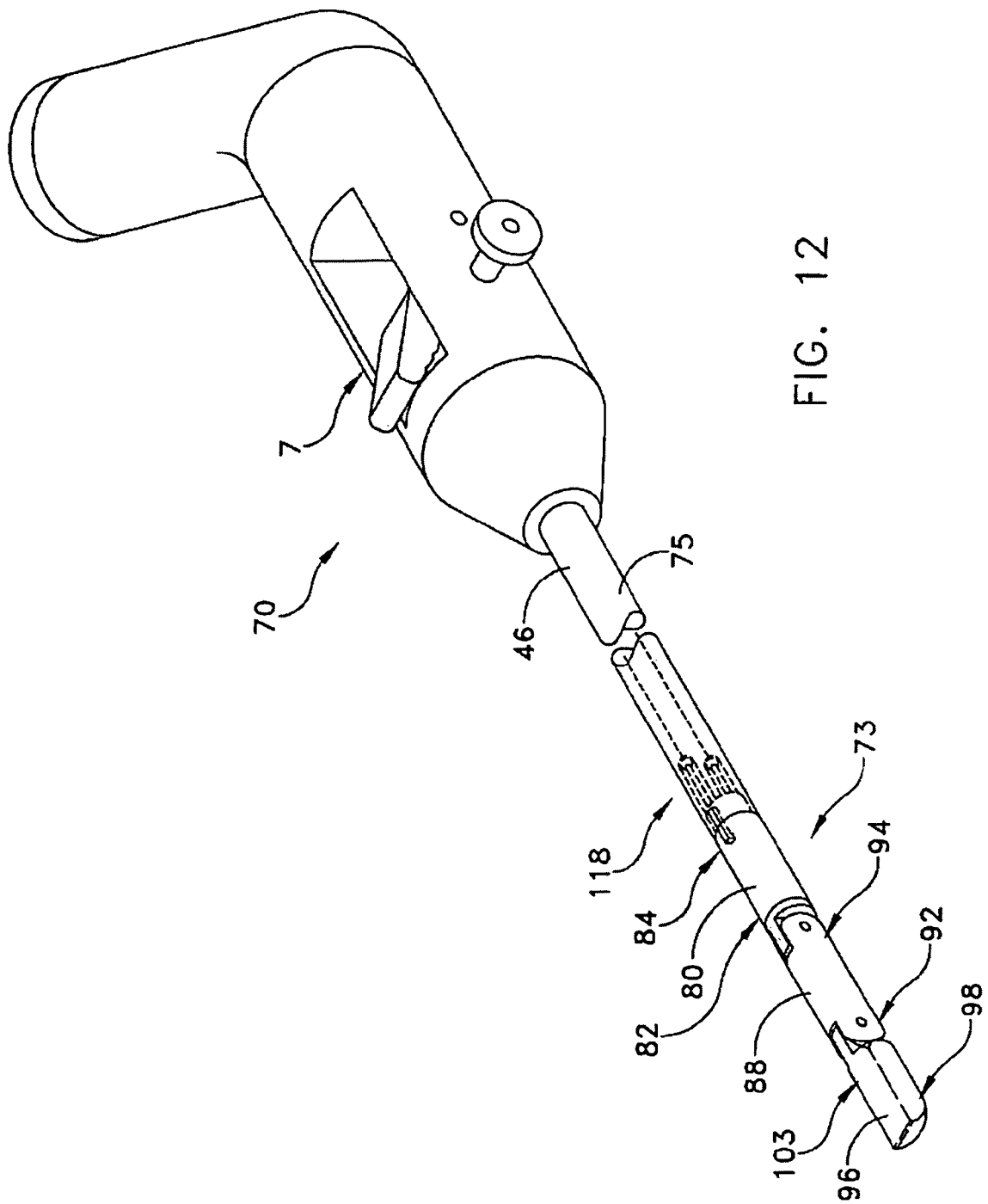
FIG. 12 is a perspective view, partially in phantom and partially broken-away, of an alternative embodiment of the articulated surgical probe including a detachable and disposable articulated digit.

This range of motion of digit 3 is limited by the interactive engagement of curved proximal end 30 of distal phalanx 26 with flat distal end 22 of middle phalanx 18 and curved distal end 12 of elongate proximal phalanx 10 with curved proximal end 24 of middle phalanx 18. In the first fully extended position, the upper or dorsal portion of curved proximal end 30 of distal phalanx 26 is blocked from further pivotal rotation by the upper or dorsal portion of flat distal end 22 of middle phalanx 18, and the upper or dorsal portion of curved distal end 12 of elongate proximal phalanx 10 is blocked from further pivotal rotation by the upper or dorsal portion of curved proximal end 24 of middle phalanx 18. Likewise, in the final flexed or crook position, the lower or anterior portion of curved proximal end 30 of distal phalanx 26 is blocked from further pivotal rotation by the lower or anterior portion of flat distal end 22 of middle phalanx 18 and the lower or anterior portion of curved distal end 12 of elongate proximal phalanx 10 is blocked from further pivotal rotation by the lower or anterior portion of curved proximal end 24 of middle phalanx 18. Thus digit 3 can be operated so as to simulate or mimic the range of movements and configurations of a surgeon's finger 42, while at the same time, maintaining a kinesthetic relationship between the surgeon's finger 42 and digit 3 (FIGS. 9 and 10). In other words, the surgeon's perception or sensing of the motion, weight, and position of digit 3, relative to the tissue being probed, is maintained as the muscles, tendons, and joints of the surgeon's finger 42 move. For example, spring and damper sensations may be sensed by the surgeon when actuating articulated digit 3 so as to palpate a vein or a mass lodged in a bowel wall or muscle structure.

Figure 4:
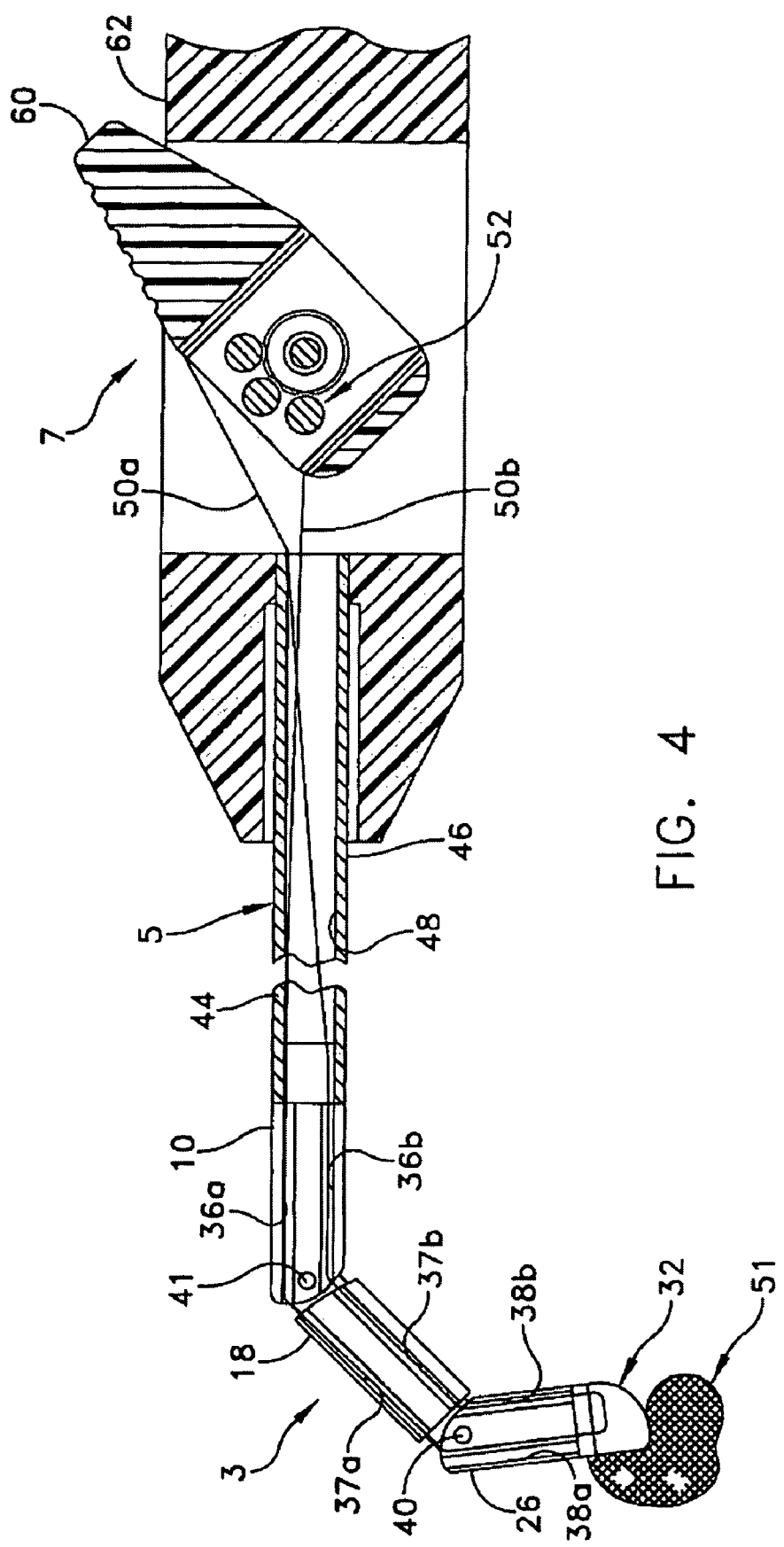
FIG. 4 is a further broken-away cross-sectional view of the articulated surgical probe of FIG. 1, including a so-called "peanut" gauze wad dissection implement assembled to a bulbous tip of an articulated digit.
Figure 5B:
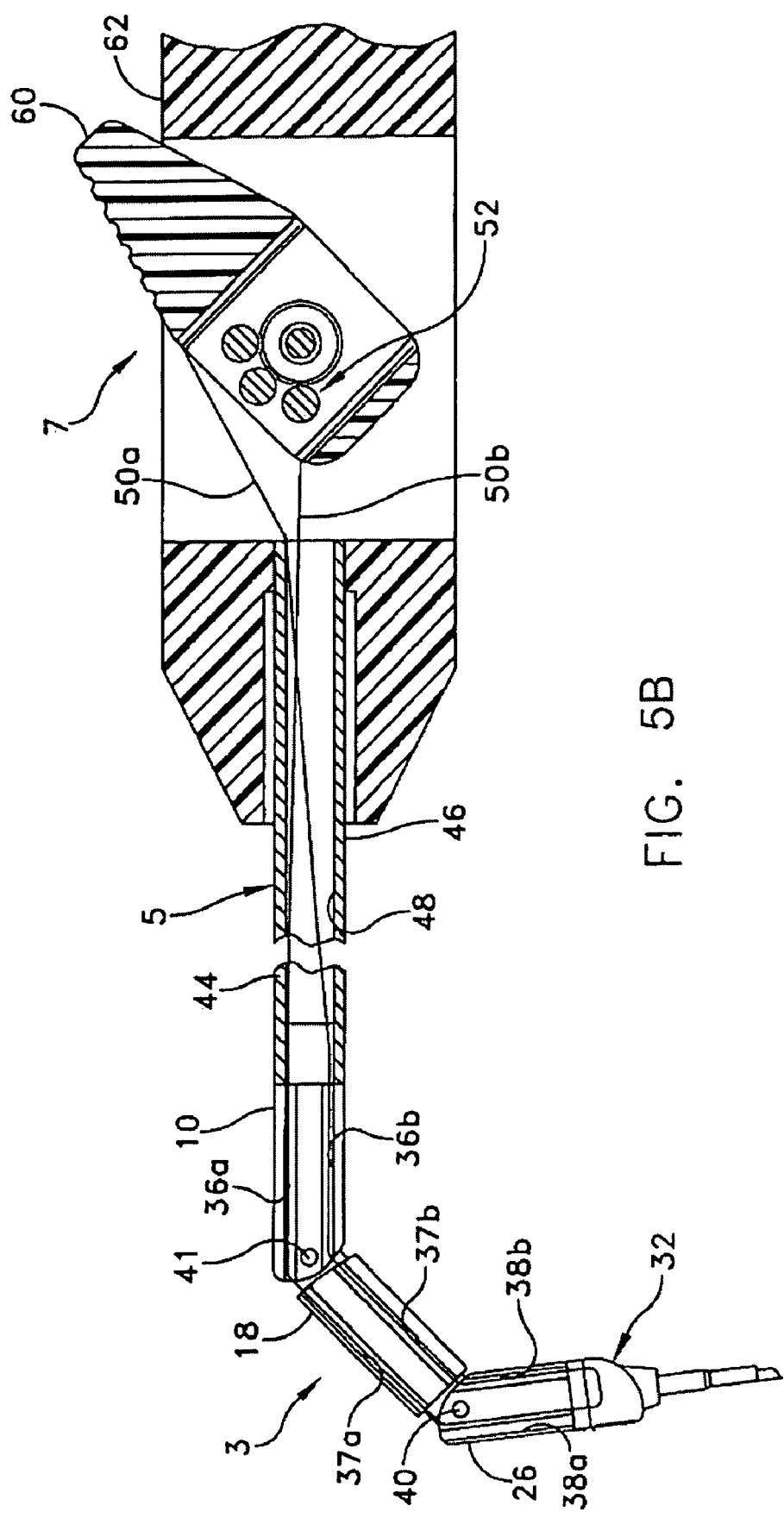
FIG. 5b is a cross-sectional view, similar to that of FIG. 5, but including a cautery tool disposed at the tip of the articulated digit.
Figure 6:
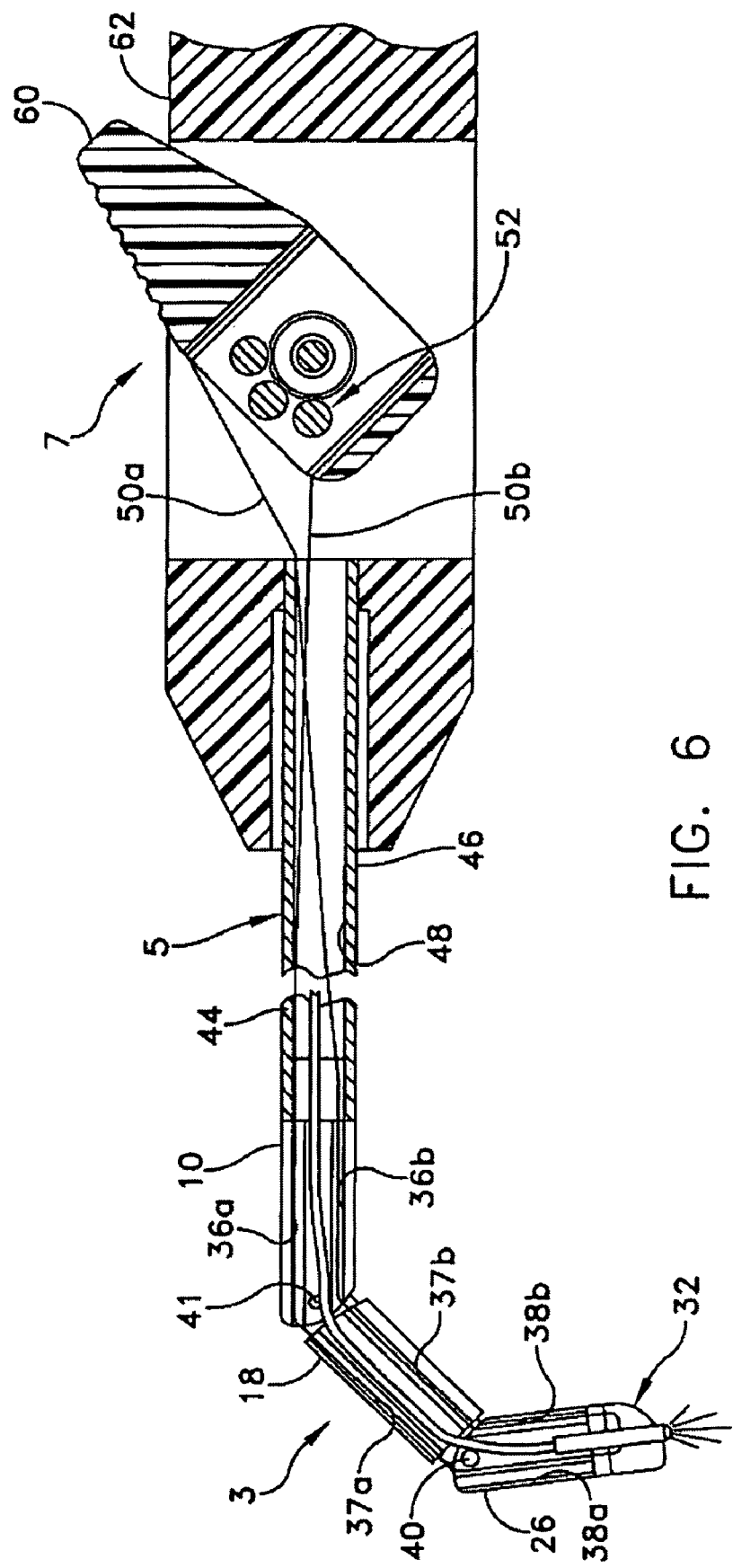
FIG. 6 is a broken-away cross-sectional view similar to FIGS. 4-5, showing a light source protruding from a tip of the articulated digit.
Figure 7:
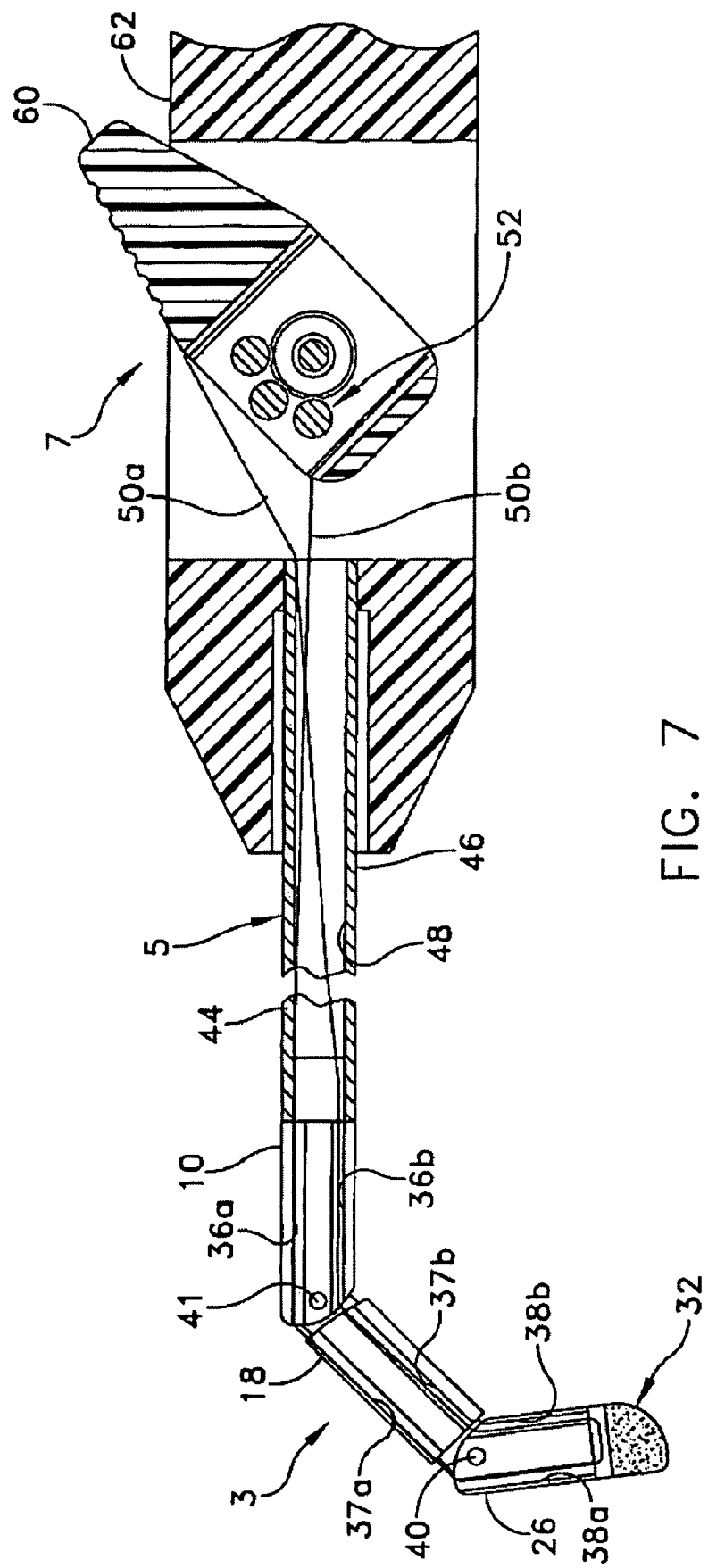
FIG. 7 is a broken-away cross-sectional view similar to FIGS. 4-6, showing an abrasive surface disposed upon a bulbous tip of the articulated digit.
Figure 8:
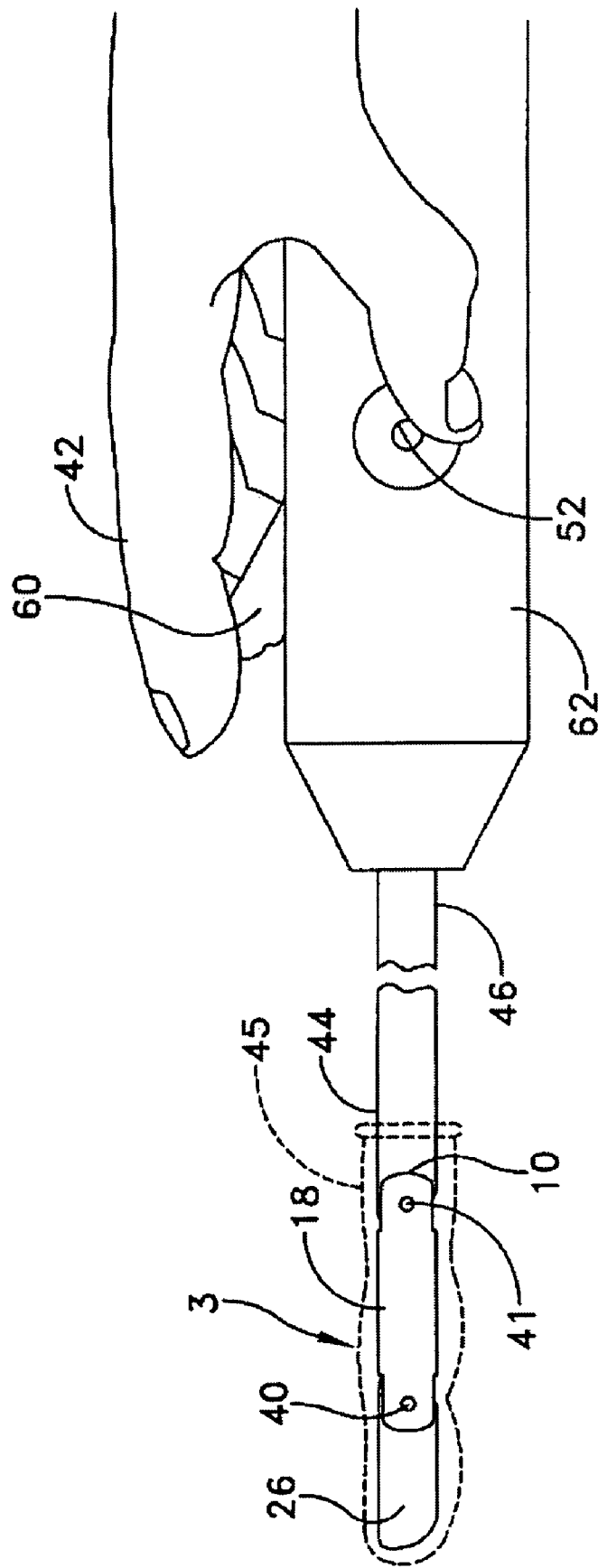
FIG. 8 is a side elevational view of an articulated surgical probe similar to that shown in FIG. 1, and illustrating the correspondence between a surgeon's finger, a toggle actuator, and an extended position of an articulated digit.

Bulbous probe-tip 32 projects outwardly from distal end 28 of distal phalanx 26 so as to provide a tactile pad or surface 29 for use in manipulating, palpating or dissecting tissue during surgery (FIGS. 4-7). Each phalanx, along with bulbous probe-tip 32, may be coated with either a compliant covering 45 that simulates the tissue of a human finger, e.g., a biocompatible elastomeric polymer, latex, or the like, a stiff and unyielding material, e.g., surgical steel or bio-grade polymers of the type well known in the art, or a combination of both materials. In addition, digit 3 may be covered with a biocompatible elastomeric polymer, latex, or the like covering sheath so as to better approximate the diameter, contour, and shape of a human finger. In one embodiment, a dorsal portion of digit 3 or bulbous probe-tip 32 is adapted to receive and hold a so-called "peanut", i.e., a sponge or gauze wad 51, so as to replicate this open surgery dissection technique (FIGS. 4-5). Also a simple "sponge" for more blunt dissection or pressure applications, can also fit into the dorsal portion of digit 3 or bulbous probe-tip 32. In addition, a detachable peanut dissector tip may also be employed (FIG. 5a). In yet another embodiment, bulbous probe-tip 32 may include a cautery attachment (FIG. 5a) to allow direct tissue cautery at bleeding points. Tissue planes may be dissected by teasing apart or pushing or pulling with various portions of digit 3, particularly bulbous probe-tip 32 which is shaped and sized so as to prevent inadvertent puncture of mesentery during manipulations or palpations. Also, a light source, e.g., a fiber optic light, L.E.D., or the like, may be placed at bulbous probe-tip 32 (FIG. 6). This extra light can illuminate narrow dark passages or transilluminate bowel mesentery, facilitating dissection and/or division of the mesentery of a portion of intestine. Bulbous probe-tip 32 may be formed so as to have either a smooth finish or be more abrasive, for more blunt dissection (FIG. 7). The entire device can be made for bariatric surgical use and would be longer at, perhaps 45 cm. Also the device can be made thinner, for delicate dissection or for pediatric surgical applications as required without deviating from the scope of the invention.

Positioning shaft 5 comprises an elongate tube having a distal end 44, a proximal end 46, and a central passageway 48 (FIGS. 2-7). In one embodiment of the invention, actuator 7 includes a pair of crossed wires 50a,50b that each extend through radially spaced-apart, longitudinally oriented through-bores 36a,36b, 37a, 37b, 38a,38b of elongate proximal phalanx 10, middle phalanx 18, and distal phalanx 26, and are each terminated to a portion of a toggle lever 60 in a handle 62 and within distal phalanx 26. When toggle lever 60 is pivoted relative to handle 62 so as to move or pivot in alignment with longitudinal axis 43, i.e., travel in a plane containing longitudinal axis 43, one of crossed wires 50a,50b is placed in tension while the other is released from tension. In this way, articulated phalanxes 10, 18, and 26 are pivoted about their respective pivot connections so as to cause digit 3 to move continuously from a substantially extended configuration to a substantially flexed, curved shape. As a result, digit 3 may be articulated so as to match a variety of finger positions normally used by a surgeon during open surgical procedures. Advantageously, digit 3 cannot bend backward, i.e., in a dorsal direction beyond parallel with longitudinal axis 43, but instead moves continuously from a first, extended position, that is often substantially longitudinally aligned with positioning shaft 5, and a second substantially curved flexed position where bulbous probe-tip 32 is located adjacent to proximal phalanx 10. The in-line or longitudinally aligned relationship of articulated digit 3, positioning shaft 5, wires 50a,50b, and actuator 7 provide for significantly improved tactile feedback. In particular, the longitudinally aligned relationship between actuator 7, positioning shaft 5, and articulated digit 3 provides a surgeon force feedback or tactile feedback, via the portion of wire 50a,50b that are in tension, and more generally known as "haptic feedback", that yields physical sensations which are felt by the surgeon while manipulating articulated digit 3 via toggle 62. A lock 52 may be incorporated in handle 62 so that toggle 60, and thereby articulated digit 3, may be locked in a desired position.

Referring to FIGS. 12-15, an alternative embodiment of articulated surgical probe 70 that comprises a detachable articulated digit 73, a positioning shaft 75 and an actuator assembly 7 that is substantially similar to that used with articulated surgical probe 1. More particularly, detachable articulated digit 73 includes an elongate proximal phalanx 80 having a distal end 82 and a proximal end 84, a middle phalanx 88 having a distal end 92 and a proximal end 94, a distal phalanx 96 having a distal end 98 and a proximal end 103, a linking assembly 106, and a bulbous probe-tip 32 (FIGS. 12-14 and 3). Proximal phalanx 80, middle phalanx 88, and distal phalanx 96 are substantially similar in construction and assembly to proximal phalanx 10, middle phalanx 18, and distal phalanx 26, and each also includes a pair of radially spaced-apart, longitudinally oriented through-bores (not shown) that are substantially similar to 36a,36b, 37a, 37b, and 38a,38b. Additionally, proximal phalanx 80 includes a mounting hub 110 that projects outwardly from proximal end 84. Mounting hub 110 is often hollow with a cylindrical shape and a smaller outer diameter than proximal phalanx 80. A blind recess 111 is defined in the outer surface of proximal end 84, adjacent to the intersection of mounting hub 111 and proximal phalanx 80.

Figure 15:
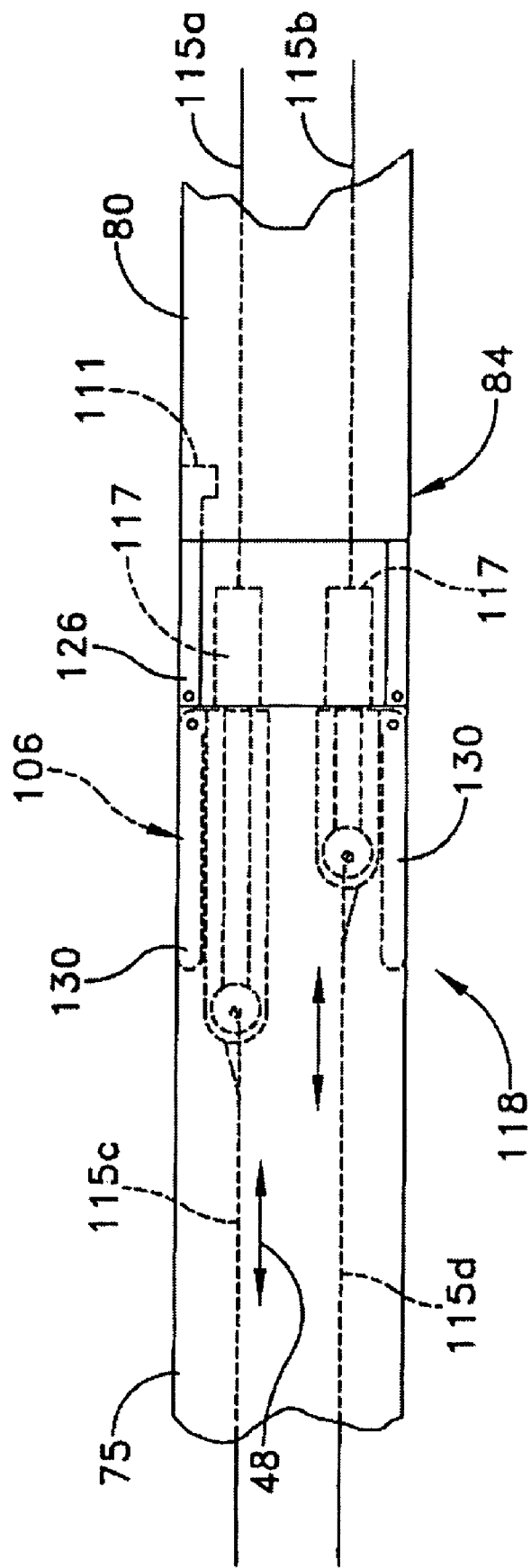
FIG. 15 is a broken-away side elevational view of the interface region of the distal portion if the articulated surgical probe shown in FIGS. 12-14.
Figure 16:
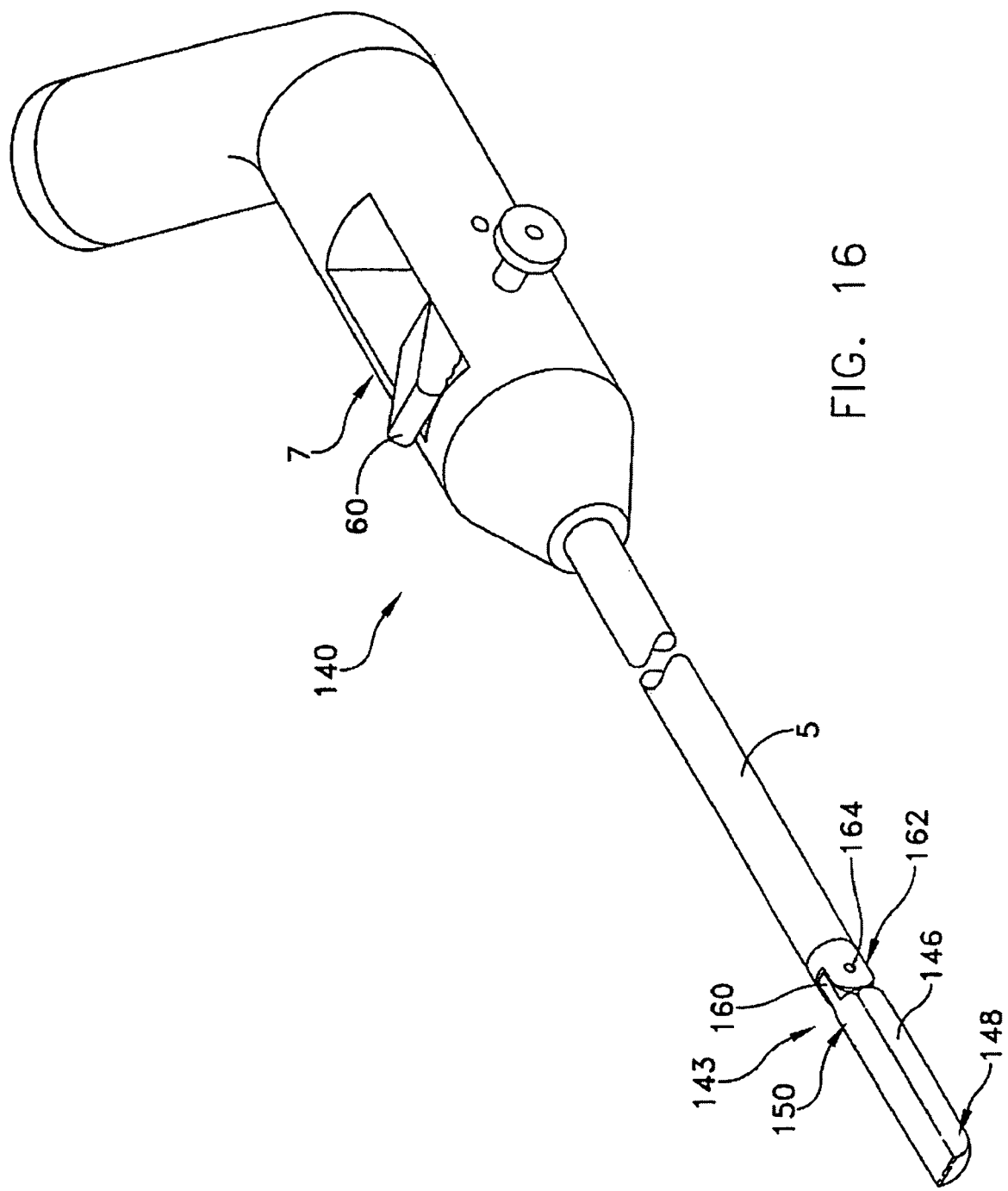
FIG. 16 is a perspective view, partially broken-away, of another alternative embodiment of the articulated surgical probe including a single phalange articulated digit.
Figure 17:
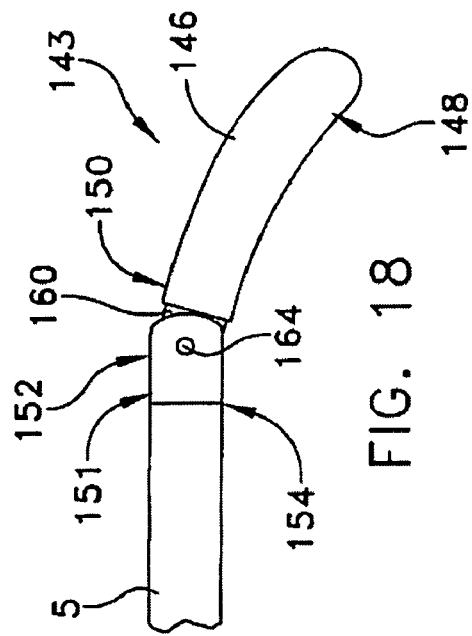
FIGS. 17-20 are broken-away side elevational views of the single knuckle articulated digit of FIG. 16, illustrating its range of motion.
Figure 18:
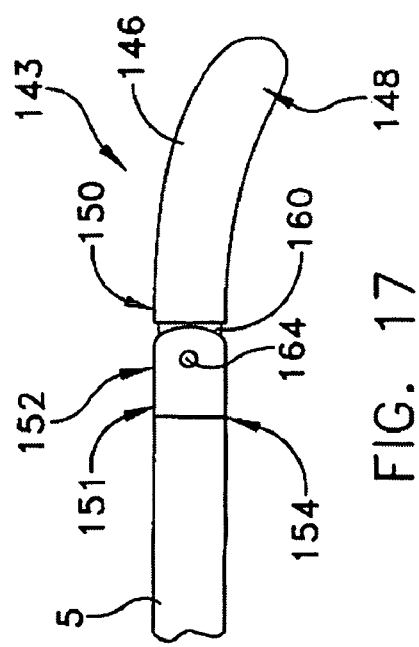
Figure 19:
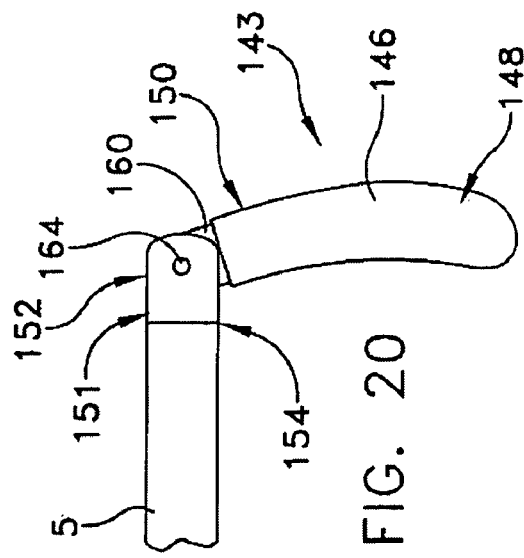
Figure 20:
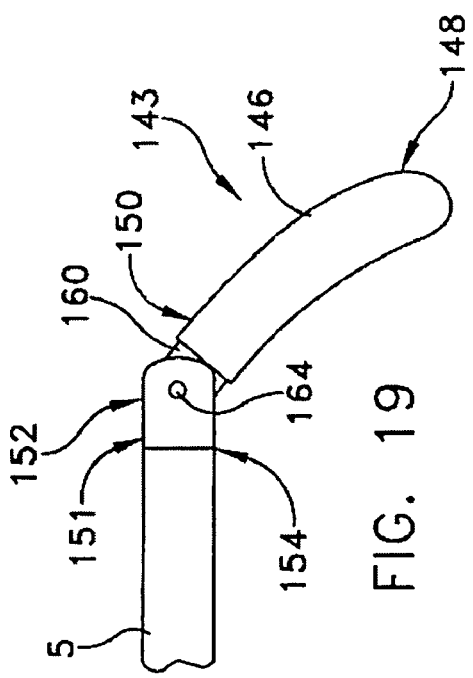

Referring to FIGS. 13-15, linking assembly 106 includes a pair of wires 115a,115b that each extend through the radially spaced-apart, longitudinally oriented through-bores located within elongate proximal phalanx 80, middle phalanx 88, and distal phalanx 96, where each are terminated to an inner portion of distal phalanx 96. A terminal 117 is fastened to the end portion of each of wires 115a,115b that extends from within mounting hub 110. Each terminal 117 includes a releasable mounting knob 119 at a mating end 120. Positioning shaft 75 comprises an elongate tube having a distal end 118, a proximal end 46, and a central passageway 48. A pair of crossed wires 115c,115d extend through central passageway 48 from actuator assembly 7 to a position adjacent to an open end 121 of positioning shaft 75. A receptacle 122 is fastened to the end portion of each of wires 115c,115d, with each receptacle 122 including a releasable mounting socket 124 that is sized and shaped to receive and releasably grasp each releasable mounting knob 119 at mating end 120 of each terminal 117. A pivotable shaft lock 126 is located on an outer surface of positioning shaft 75 adjacent to open end 121, and a pair of pivotable receptacle clamps 130 are arranged on the outer surface of positioning shaft 75 at a location corresponding to the location of releasable mounting sockets 124 within central passageway 48.

Detachable articulated digit 73 may be fastened to positioning shaft 75 of articulated surgical probe 70 by first arranging proximal end 84 of proximal phalanx 80 in confronting coaxial relation with open end 121 of positioning shaft 75. Once in this position, articulated digit 73 is moved toward positioning shaft 75 so that mounting hub 110 slips into open end 121 and central passageway 48 of positioning shaft 75. As this occurs, each terminal 117 on wires 115a and 115b are received within a corresponding receptacle 122 so that each releasable mounting knob 119 at mating end 120 engages a releasable mounting socket 124. Once mounting hub 110 is fully received within open end 121 of positioning shaft 75, pivotal shaft lock 126 is pivoted about its position on the outer surface of positioning shaft 75 until it engages blind recess 111 in the outer surface of proximal end 84 of proximal phalanx 80. Each pivotable receptacle clamp 130 is then actuated so as to releasably clamp each mounting knob 110 within its respective mounting socket 124 thereby completing the operative interconnection of wires 115a, 115b, 115c and 115d. With detachable articulated digit 73 fully engaged with positioning shaft 75, operation of articulated surgical probe 70 follows in accordance with the operation of articulated surgical probe 1.

As with articulated digit 3, the phalanges of detachable digit 73 may pivot relative to one another so that articulated digit 73 comprises a range of motion that is continuous between a first fully extended position that may be, for example, aligned with the longitudinal axis of positioning shaft 75, and often substantially coaxial with positioning shaft 75, and a final substantially curved, flexed, crook, or "hook-shaped" position, i.e., curved or bent relative to positioning shaft 75. Thus digit 73 can be operated so as to simulate the range of movements and configurations of a surgeon's finger 42, while at the same time, maintaining a kinesthetic relationship between the surgeon's finger 42 and articulated digit 73. The surgeon's perception or sensing of the motion, weight, and position of articulated digit 73, relative to the tissue being probed, is maintained as the muscles, tendons, and joints of the surgeon's finger 42 move.

Figure 21:
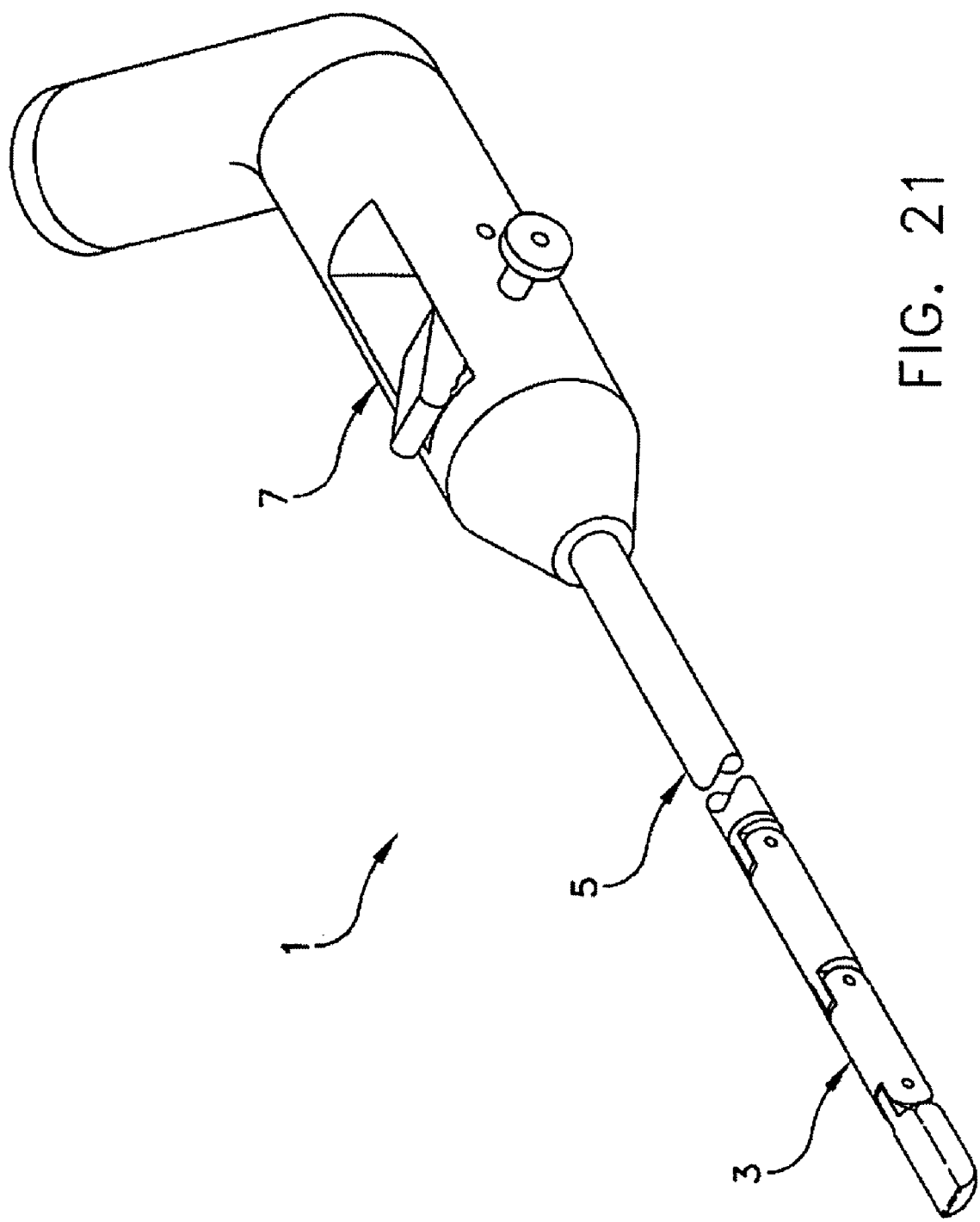
FIG. 21 is a perspective view of an articulated surgical probe formed in accordance with another embodiment of the invention having an articulated digit with a plurality of phalanges.

Referring to FIGS. 16-20, a further alternative embodiment of articulated surgical probe 140 comprises a single phalange digit 143, a positioning shaft 5 and an actuator assembly 7. The construction and arrangement of positioning shaft 5 and actuator assembly 7 are substantially similar to that used with articulated surgical probe 1. Single phalange articulated digit 143 includes an elongate proximal phalanx 146 having a distal end 148 and a proximal end 150, and a distal phalanx 151 having a distal end 152 and a proximal end 154. Proximal phalanx 146 comprises a blade hinge 160 that projects longitudinally outwardly from proximal end 150, and also includes a pair of radially spaced-apart, longitudinally oriented internal blind-bores (not shown) arranged in similar manner to radially spaced-apart, longitudinally oriented through-bores 36a, 36b of articulated digit 3 (FIGS. 2-7). Distal phalanx 151 comprises a yokel 62 that is sized and arranged on the distal end of positioning shaft 5 so as to receive blade hinge 160. Yoke 162 is pivotally fastened to blade hinge 160 by a pivot pin 164. In this way, proximal phalanx 146 may pivot relative to distal phalanx 151 so that single knuckle digit 143 comprises a range of motion that is continuous between a first fully extended position that may be, for example, aligned with the longitudinal axis of positioning shaft 5, and often substantially coaxial with positioning shaft 5, and a final substantially, flexed position, i.e., bent relative to positioning shaft 5. Referring to FIG. 21, an articulated surgical probe may also be formed in accordance with another embodiment of the invention having an articulated digit 3 comprising three, four or a plurality of phalanges without departing from the scope or spirit of the present invention.

It should be understood that, although less preferred, the toggle lever and wire assembly of articulated surgical probes 1, 70, and 140 may be replaced by a motorized motivator, e.g., a miniature servo-motor, of the type well known in the art, so long as, the kinesthetic relationship between the surgeon's actuating finger 42 and the articulated digit 3, 74, or 143 are maintained. Alternatively, and now referring to FIGS. 21-23, actuator assembly 7 comprising a toggle lever 60 and wires 50a, 50b may be replaced by a toggle lever 60 and linkage assembly 170 to form an operative connection to an articulated digit 173. More particularly, articulated surgical probe 172 includes articulating digit 173 located at distal end 44 of positioning shaft 5. More particularly, articulating digit 173 includes an elongate, hollow proximal phalanx 178 having a distal end 180 and a proximal end 182, a hollow middle phalanx 184 having a distal end 186 and a proximal end 188, and a hollow distal phalanx 190 having a distal end 192 and a proximal end 193. Proximal end 180 of proximal phalanx 178, includes a pair of spaced apart, diametrically confronting hinge arms 198a,198b that project longitudinally outwardly from proximal end 182. Each of hinge arms 198a, 198b defines a through-hole sized to receive a corresponding hinge pin 200. Middle phalanx 184 includes two pair of hinge arms 202a,202b and 203a,203b that project longitudinally outwardly from each of proximal end 188 and distal end 186, while distal phalanx 190 includes a single pair of hinge arms 204a,204b that project longitudinally outwardly from proximal end 193. Each of hinge arms 202a,202b, 203a,203b, and 204a,204b define a through-hole sized to receive a corresponding hinge pin 200.

Figure 22:
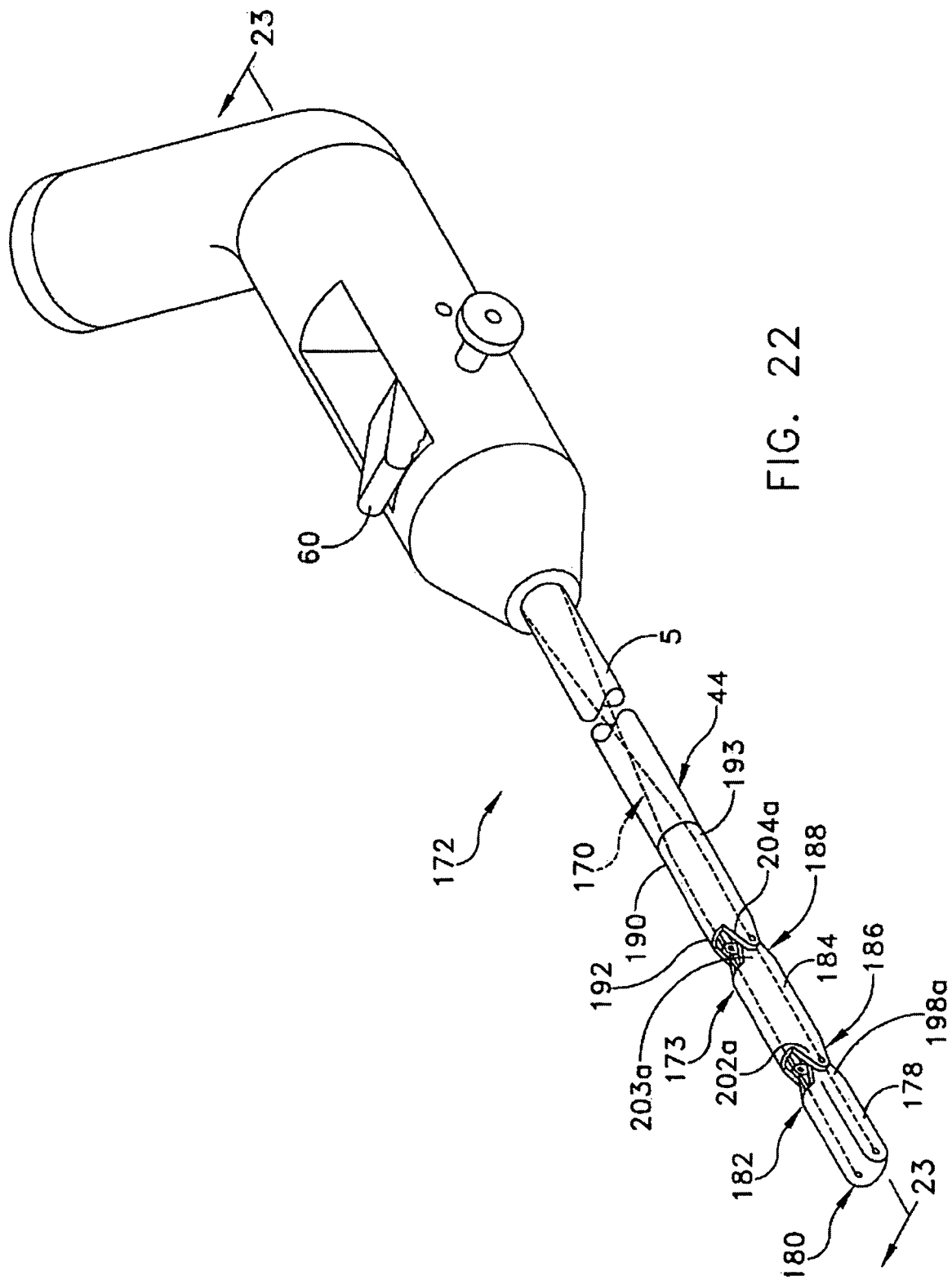
FIG. 22 is a perspective view, partially in phantom and partially broken-away, of yet another alternative embodiment of the articulated surgical probe formed in accordance with the present invention.

Referring to FIGS. 22 and 23, linkage assembly 170 is operatively positioned within, and extends throughout the interior of each of proximal phalanx 178, a hollow middle phalanx 184, and a hollow distal phalanx 190, and comprises a plurality of dorsal links 207a, 207b, 207c, a plurality of anterior links 208a, 208b, 208c, and at least two cross-links 209a,209b. Each of dorsal links 207a, 207b, 207c and anterior links 208a, 208b, 208c comprises a pair of longitudinally spaced apart holes that are sized so as to accept a hinge pin 210, while each of cross-links 209a,209b comprises three longitudinally spaced apart holes. The outer most two of which are sized so as to accept a hinge pin 210, with a centrally located hole sized to accept hinge pin 200. Anterior link 208c and dorsal link 207c cross one another, and are each pivotally terminated to a portion of the interior of toggle lever 60 in handle 62, and within a portion of the interior of hollow distal phalanx 190. Once again, when toggle lever 60 is pivoted relative to handle 62 so as to move or pivot, one of crossed anterior link 208c and dorsal link 207c is placed in tension while the other is released from tension. In this way, articulated phalanxes 178, 184, and 190 are pivoted about their respective pivot connections, via toggling of cross-links 209a,209b caused by the relative longitudinal movements of dorsal links 207a, 207b, 207c and anterior links 208a, 208b, 208c, so as to cause articulated digit 172 to move continuously from a substantially extended configuration to a substantially flexed, curved shape.

As with articulated digit 3, when articulated digit 173 is in a first fully extended position, the upper or dorsal portion of the proximal end of distal phalanx 190 is blocked from further pivotal rotation by the upper or dorsal portion of the distal end of middle phalanx 184, and the upper or dorsal portion of the distal end of proximal phalanx 178 is blocked from further pivotal rotation by the upper or dorsal portion of the proximal end of middle phalanx 184. Likewise, in a final flexed or crook position, the lower or anterior portion of the proximal end of distal phalanx 190 is blocked from further pivotal rotation by the lower or anterior portion of the distal end of middle phalanx 184, and the lower or anterior portion of the distal end of proximal phalanx 178 is blocked from further pivotal rotation by the lower or anterior portion of the proximal end of middle phalanx 184.

ADVANTAGES OF THE INVENTION

Numerous advantages are obtained by employing the present invention. The position of any of articulated digits 3, 74, 143, or 173 in, e.g., the abdomen of a patient, is mirrored by the position of the surgeon's finger 42 on toggle 60 (FIGS. 2-3) with the extent and types of motion being quite similar. Because the configuration of articulated digit 3, 74, 143, or 173 transitions in a manner that is very similar to a surgeon's finger, various dissecting maneuvers, not possible with existing small tipped instruments, can be accomplished. Bolder, longer, and firmer movements, as in open surgery can be done, with these movements taking less time than more tedious slower, smaller movements, as with available small tipped instruments.

Figure 25:
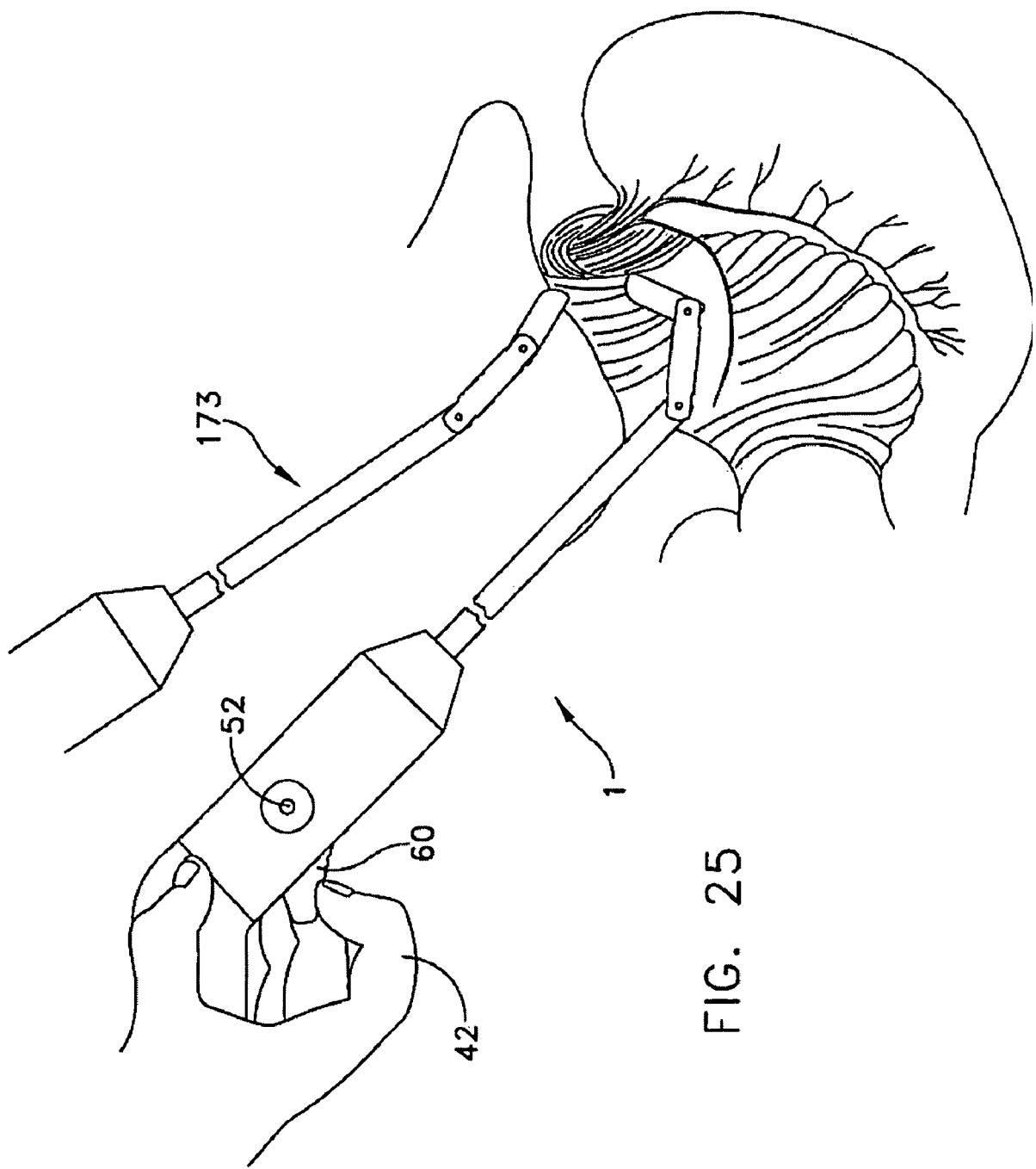
FIG. 25 is a side perspective view, partially broken-away, showing one method of interaction between two articulated surgical probes a portion of a liver and a portion of an esophagus.
Figure 26:
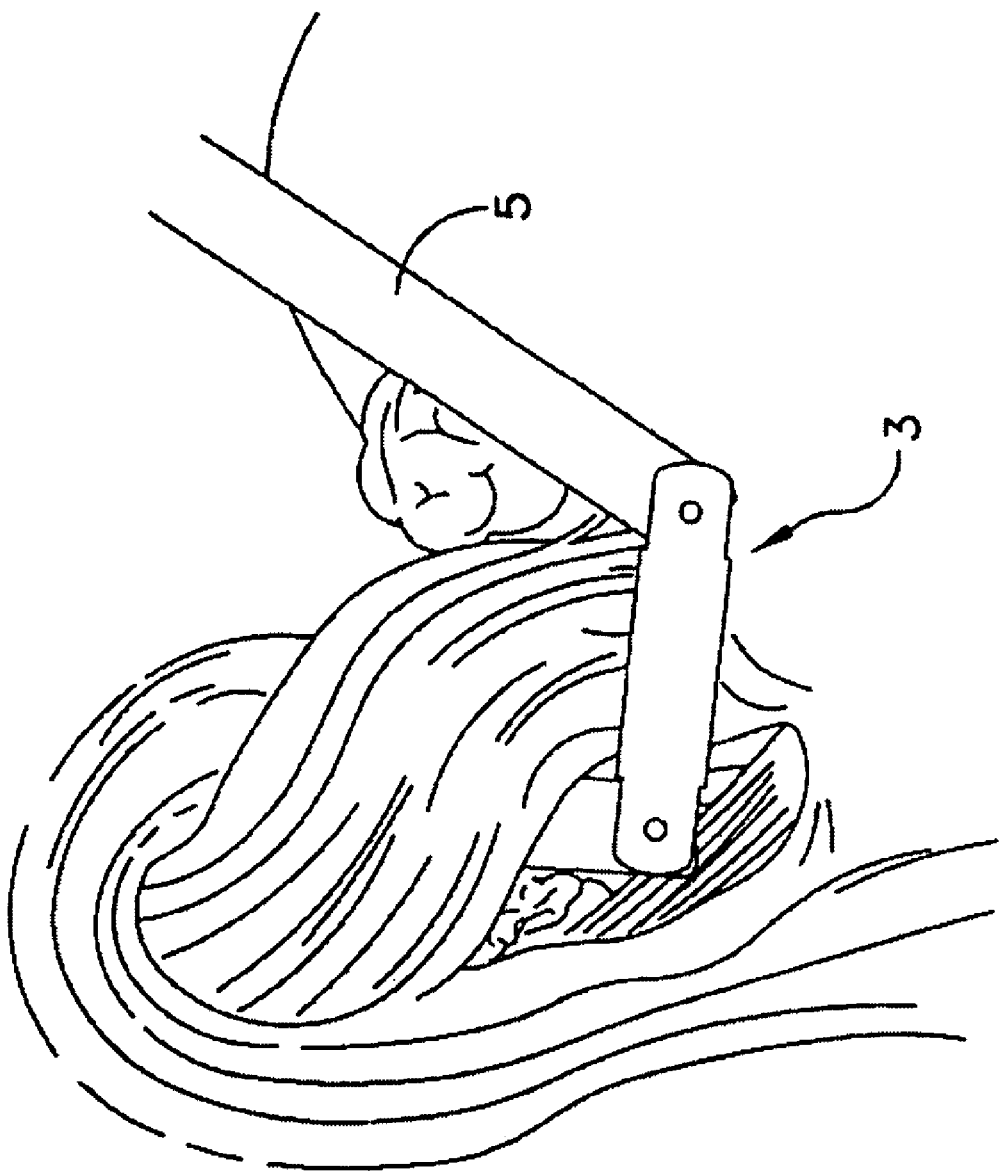
FIG. 26 is a side perspective view, partially broken-away, showing an enlarged view of the interaction between an articulated surgical probe of the present invention and a portion of an esophagus.
Figure 27:
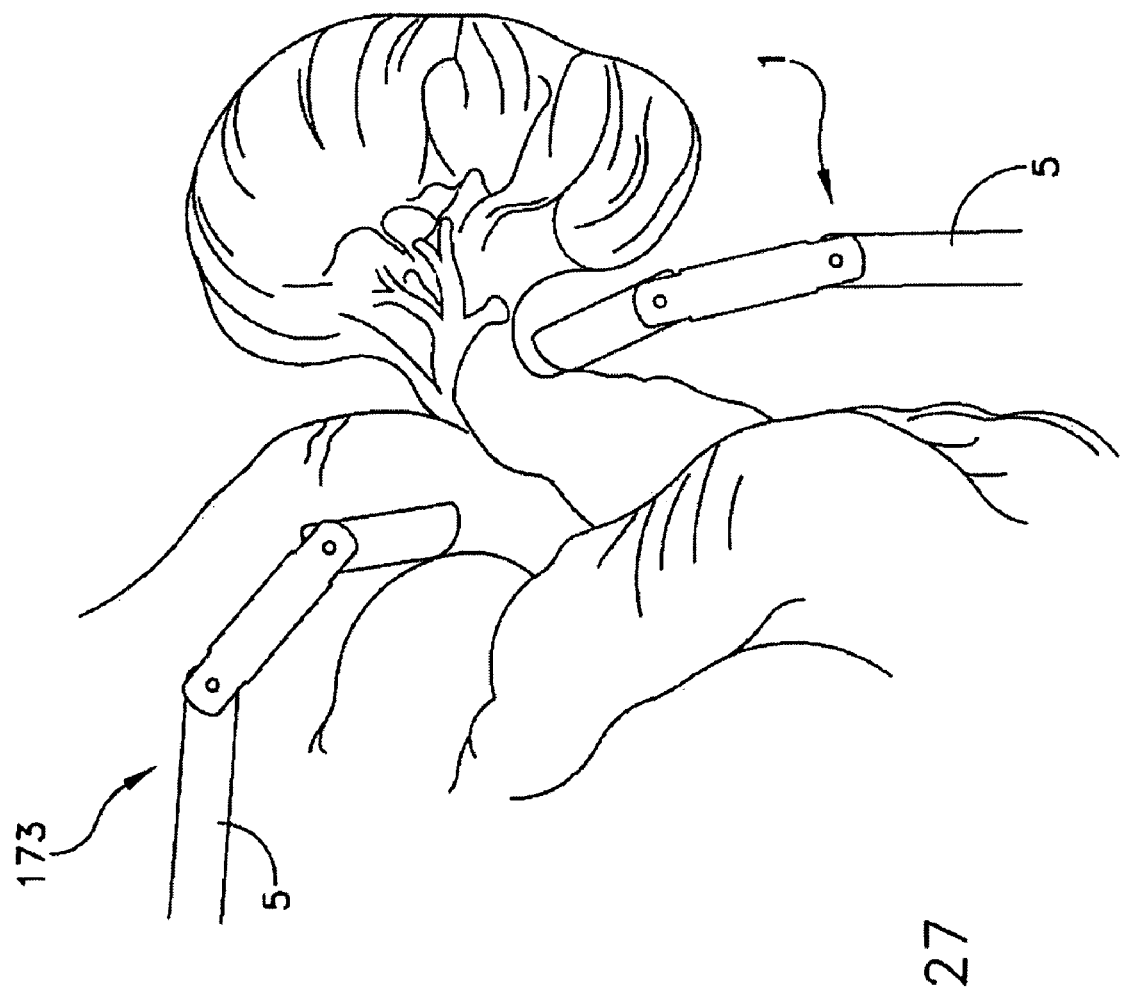
FIG. 27 is a side perspective view, partially broken-away, showing one method of interaction between two articulated surgical probes and a portion of a spleen.
Figure 28:
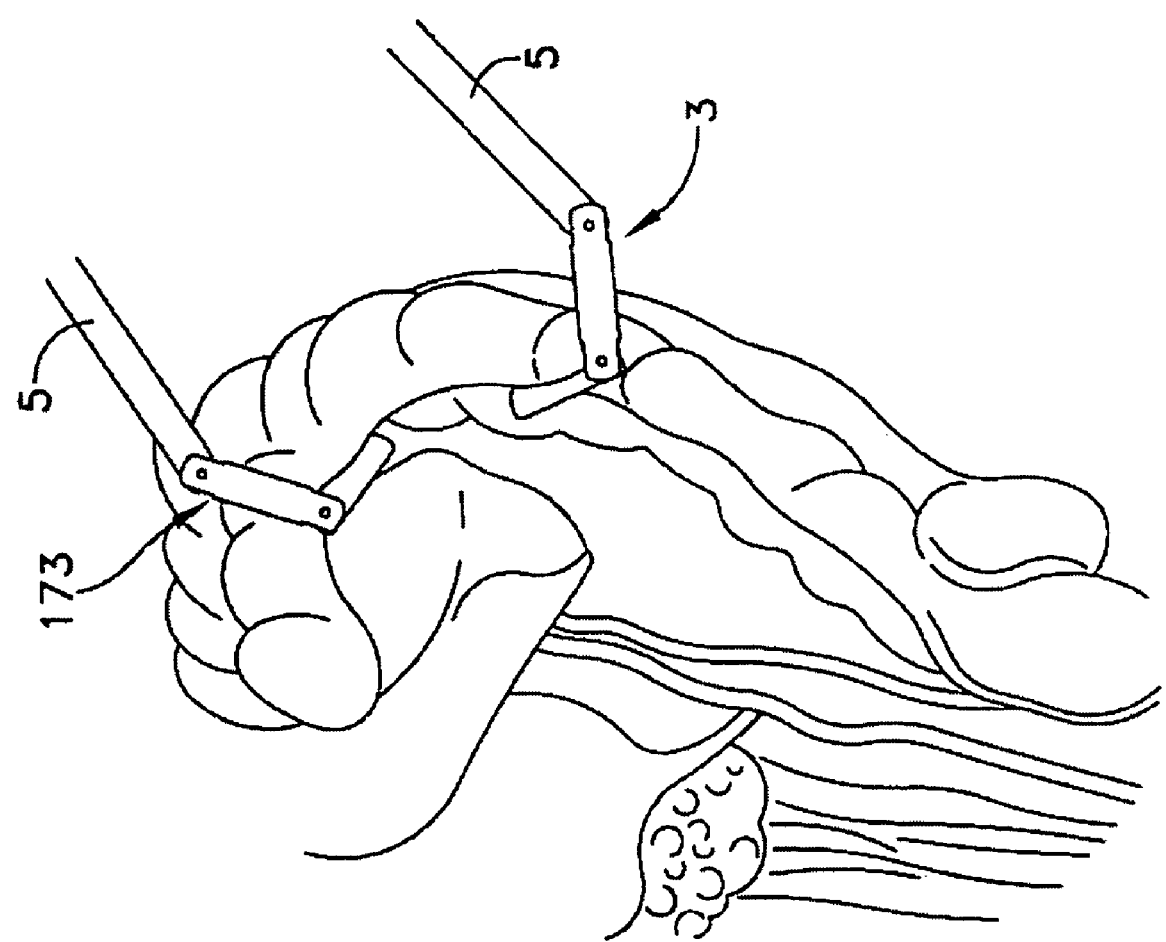
FIG. 28 is a side perspective view, partially broken-away, showing another method of interaction between two articulated surgical probes and portion of bowel.

For example, with a laparosopic approach it is often difficult and time consuming to dissect around certain structures compared to open surgery. Dissection around the esophagus (FIGS. 24 and 25), around the splenic hilar vessels (FIG. 26) or bowel (FIG. 27) is tedious when small-tipped instruments are used, however, articulated surgical probes 1, 70, or 140 are able to duplicate or at least approximate the finger positions and movements associated with an open surgical approach, and therefore facilitates dissection of such structures. For example, minimally invasive dissection of adherent omentum will be similar to open surgery when operating an articulated surgical probe formed in accordance with the present invention in either hand, with retraction, pushing, and pulling of the omentum being done substantially as efficiently as in open surgery.

Advantageously, an articulated surgical probe formed in accordance with the foregoing preferred embodiments may be actuated so as to apply a variable amount of force to its articulated digit by flexing and or pulling or pushing the entire device (FIG. 24-27). This often is important, e.g., when holding the stomach or colon away from a surgical site is needed (retracting) so as to enable dissection. It is well known that prior art devices often cause tears in the otherwise healthy tissue further complicating the procedure, because such prior art small tipped instruments tend to be sharp or pointed. Articulated digit 3, 73, 143, or 173 allows for more blunt retraction of such obstructing tissue. Articulated surgical probe 1 also allows dissection movements similar in range to a surgeon's finger. Compared to hand assisted laparoscopy, articulated digit 3 allows dissection without the rest of the surgeon's hand blocking the view of the operative field on the monitor screen. In one embodiment, two articulated surgical probes 1 and 100 may be used through two incision ports so as to provide even greater range of tissue manipulation with an unobstructed view, when compared to hand assisted surgery.

Articulated surgical probe 1 allows dissection movements similar in force to a surgeon's finger. The force applied by articulated digit 3, 73, 143, or 173 can be from very gentle, subtle movements to firm, strong dissection. Gentle movement is often necessary near blood vessels or tenuous tissues. Stronger dissection, for example, is necessary to peel the rectum away from the sacrum. Both types of procedures may be done without any structural change being made to articulated surgical probes 1, 70, or 140. Articulated surgical probes 1, 70, or 140 additionally provide for increased retraction, when digit 3, 73, 143, or 173 is flexed, as compared to a straight prior art instrument. In this technique, handle 62 remains relatively parallel to the patient's body, e.g., the abdominal wall. In contrast, with a straight prior art instrument, when retracting the stomach, for example, the prior art handle must be levered to about 90 degrees in order to enable the same amount of retraction.

In prior art dissection procedures, viscera is often retracted with stiff grasping tools. This can cause inadvertent tearing of the bowel, which may require surgical repair. Articulated surgical probe 1 also provides for gentle but secure retraction of viscera when in either a locked or unlocked position. Gentle retraction of soft parts of viscera is essential to avoid inadvertent damage. Because there is tactile feedback resulting from the straight, in-line relation between handle 62, positioning shaft 5, and digit 3, 73, 143, or 173, the retracting or dissecting with digit 3, 73, 143, or 173 is less apt to cause damage than the straighter, less tactile, instruments of the prior art. Furthermore, the present invention is less apt to cause damage than prior art small tipped instruments of the prior art which often do not transmit forces directly to the surgeon, and often have sharp tips.

A locked position, via actuation of locking mechanism 52, allows the surgeon to hold articulated surgical probe 1 anywhere along the instrument, so that hand fatigue can be avoided. The unlocked position allows for multiple changes as to where the viscera is held for retraction, during dissection. Countertraction of tissue or viscera can be accomplished with articulated surgical probe 1 as well. This countertraction, i.e., away from the point of dissection, is part of the traction-countertraction action inherent to open surgical maneuvers, and difficult with prior art small tipped laparoscopic instruments.

Advantageously, articulated surgical probe 1 allows palpation of masses, such as tumors inside the colon, with bulbous probe-tip 32. The tactile feed-back provided by the in-line relationship of handle 62, positioning shaft 5, wires 50a,50b, and digit 3 helps direct a surgeon as to the margins of resection of a tumor. Otherwise, a section of intestine could be removed without encompassing the tumor. In current minimally invasive surgery, this is only discovered upon opening the specimen after it is removed from the patient.

In some instances, dissection of structures, such as the gallbladder from the liver bed with digit 3, can copy the techniques used by the surgeon's own finger during open gall bladder dissection, e.g., peeling away the gallbladder from the liver bed. Laparoscopic dissection, particularly in difficult cases, therefore can be made faster and safer. In addition, when there is intra operative bleeding during laparoscopic surgery, it is difficult to apply direct pressure with an "end-on" application of a prior art instrument, especially if the bleeding is slightly above or below the immediate point of dissection. Since digit 3 of articulated surgical probe 1 flexes, bulbous probe-tip 32 can apply direct pressure so that bleeding can be controlled in a quicker, more reliable fashion, approximating very closely the same maneuver utilizing the surgeon's finger.

When various staplers are employed to divide intestine or stomach, tissue planes adjacent to viscera can be dissected in order to explore the anatomy with articulated surgical probe 1 or prepare an organ or organ part for removal. This manipulation is similar to what is often done in open surgery. Furthermore, the stapler distal tip may be difficult to visualize, on a television monitor. Articulated digits 3, 74, 143, or 173 of articulated surgical probes 1, 70, 140, and 172 can support the distal stapler tip so as to optimize the application angle, as well as, assure that the proper amount of intestine is lined up for the division. Inadvertent inclusion of unwanted tissue can be avoided as well as incomplete application of the stapler.

It is to be understood that the present invention is by no means limited only to the particular constructions herein disclosed and shown in the drawings, but also comprises any modifications or equivalents within the scope of the claims.

We claim:

1. A surgical probe allowing a surgeon to manipulate tissue while maintaining a kinesthetic relationship between the surgeon's finger during a surgical procedure, said probe comprising:
   an articulated digit located at a distal end of a positioning shaft having a longitudinal axis and a handle, where said articulated digit is configured to move between a continuous range of positions from an extended position to a substantially curved position such that movement of the articulated digit is similar to movement of a human finger; and
   an actuator coupled to said handle by a pivot and extending upright relative to said longitudinal axis such that the actuator is moveable between a distal position and a proximal position along said longitudinal axis; and
   where said actuator is operatively connected to said articulated digit by a plurality of link members where a proximal end of said link members are affixed to said actuator so as to move said articulated digit between said continuous range of positions, where said distal position corresponds to said extended position of said articulated digit and where said proximal position corresponds to said substantially curved position of said articulated digit where movement of said articulated digit mimics movement of the surgeon's finger and movement of said actuator to said proximal position causes a first link member to be placed in tension while a second link member is released from tension such that the surgeon maintains the kinesthetic relationship via said actuator from the link member in tension.

2. A surgical probe according to claim 1 wherein said articulated digit includes an elongate proximal phalanx having a curved distal end and a proximal end, a middle phalanx having a flat distal end and a curved proximal end, and a distal phalanx having a distal end and a curved proximal end.

3. A surgical probe according to claim 1 wherein said articulated digit includes a plurality of phalanges.

4. A surgical probe according to claim 3 wherein said phalanges comprise end features that provide for a limited pivoting relative to adjacent phalanges.

5. A surgical probe according to claim 2 wherein said proximal phalanx includes a pair of radially spaced-apart, longitudinally oriented through-bores, said middle phalanx includes a pair of radially spaced-apart, longitudinally oriented through-bores, and said distal phalanx includes a pair of radially spaced-apart, longitudinally oriented through-bores.

6. A surgical probe according to claim 2 wherein said curved proximal end of said distal phalanx is pivotally connected to said flat distal end of said middle phalanx and said curved distal end of said elongate proximal phalanx is pivotally connected to said curved proximal end of said middle phalanx so as to comprise the range of motion that is continuous between said extended position that is aligned with said longitudinal axis and said substantially curved position.

7. A surgical probe according to claim 6 wherein the range of motion of said digit is limited by an interactive, rolling engagement of (i) said curved proximal end of said distal phalanx with said flat distal end of said middle phalanx and, (ii) said curved distal end of said elongate proximal phalanx with said curved proximal end of said middle phalanx.

8. A surgical probe according to claim 6 wherein said extended position locates a dorsal portion of said curved proximal end of said distal phalanx in blocking relation with said dorsal portion of said flat distal end of said middle phalanx so as to prevent further pivotal rotation, and a dorsal portion of said curved distal end of said elongate proximal phalanx is blocked from further rolling engagement by a dorsal portion of said curved proximal end of said middle phalanx.

9. A surgical probe according to claim 6 wherein said substantially curved position locates (i) an anterior portion of said curved proximal end of said distal phalanx in blocking relation with an anterior portion of said flat distal end of said middle phalanx and, (ii) an anterior portion of said curved distal end of said elongate proximal phalanx in blocking relation with an anterior portion of said curved proximal end of said middle phalanx.

10. A surgical probe according to claim 1 wherein said articulated digit includes a rounded probe-tip.

11. A surgical probe according to claim 1 wherein said surgeon's perception of a motion, weight, and position of said articulated digit, relative to a tissue being probed, is maintained through said link member in tension as the muscles, tendons, and joints of the surgeon's finger move said actuator causing said articulated digit to move between said continuous range of positions.

12. A surgical probe according to claim 1 wherein a spring and damper sensation is transferred to the surgeon when actuating said articulated digit so as to engage tissue structure.

13. A surgical probe according to claim 10 wherein said rounded probe-tip projects outwardly from a distal end of articulated digit so as to provide a tactile pad for use in manipulating or dissecting tissue during surgery.

14. A surgical probe according to claim 1 wherein each said link member includes a plurality of links arranged in a linkage mechanism operatively connected to said digit.

15. A surgical probe according to claim 1 wherein said articulated digit comprises a tip having a gauze wad releasably fixed to a dorsal surface for dissection.

16. A surgical probe according to claim 1 wherein said articulated digit is sheathed with a polymeric material so as to better approximate the diameter, contour, and shape of a human finger.

17. A surgical probe according to claim 1 wherein said articulated digit comprises a releasable tip.

18. A surgical probe according to claim 10 wherein said bulbous tip includes at least one of a light source and a cautery.

19. A surgical probe according to claim 10 wherein said rounded tip includes an abrasive surface for blunt dissection of tissue.

20. A surgical probe according to claim 5 wherein said link members extends through said radially spaced-apart, longitudinally oriented through-bores that extend through said elongate proximal phalanx, said middle phalanx, and said distal phalanx with said at least one link member being terminated to a portion of said distal phalanx.

21. A surgical probe according to claim 20 wherein at least one link member comprises a wire.

22. A surgical probe according to claim 20 wherein movement of said actuator provides a haptic feedback through said portion of said at least one link member that is in tension so as to create physical sensations which are felt by the surgeon while manipulating said actuator.

23. A surgical probe according to claim 1 wherein said actuator includes a lock so that said articulated digit can be releasably locked in a desired position.

24. The surgical probe according to claim 1, wherein at least a portion of the handle generally axially extends from the proximal end of the shaft at an inclined angle.

25. The surgical probe according to claim 1, wherein at least a portion of the handle is rotatable relative to a remainder of the handle.

26. A surgical probe allowing a surgeon to manipulate tissue while maintaining a direct kinesthetic relationship between the surgeon's finger during a surgical procedure, said probe comprising:
an articulated digit located at a distal end of a positioning shaft having a longitudinal axis;
a handle having a first portion located in alignment with said longitudinal axis at a proximal end of the positioning shaft;
an actuator extending from a surface of said first portion of said handle and being pivotally moveable between a distal and proximal positions such that the actuator is limited to pivot in alignment with both said articulated digit and said positioning shaft and where said actuator is operatively connected to said articulated digit; and
where said actuator is operatively connected to said articulated digit by a plurality of link members where a proximal end of said link members are affixed to said actuator and where movement of said actuator to said proximal position causes a first link member to be placed in tension while a second link member is released from tension such that the link member in tension provides direct force feedback to said actuator from said articulated digit allowing the direct kinesthetic relationship between the surgeon's finger and said articulated digit as it operates said actuator.

27. A surgical probe allowing a surgeon to manipulate tissue while maintaining a direct force feedback between the surgeon's finger during a surgical procedure, said probe comprising:
an articulated digit located at a distal end of a positioning shaft having a longitudinal axis;
a handle having a first portion located at a proximal end of the positioning shaft in alignment with said axis;
an actuator extending from said first portion of said handle and coupled to said handle by a pivot to allow the surgeon to grasp said handle while extending the finger parallel to said handle and in alignment with said longitudinal axis to engage the actuator; and
where said actuator is operatively connected to said articulated digit by at least a plurality of link members where a proximal end of said link members are affixed to said actuator that provide direct force feedback to said actuator from said articulated digit as said actuator moves between said distal and proximal positions where movement of said actuator to said proximal position causes a first link member to be placed in tension while a second link member is released from tension such that the surgeon maintains the direct force feeback via said actuator from the link member in tension so as to provide at least one of a kinesthetic and a tactile relationship between said articulated digit and the surgeon's finger.

28. A surgical probe according to claim 27 wherein said articulated digit includes an elongate proximal phalanx having a curved distal end, a proximal end, and a pair of radially spaced-apart, longitudinally oriented through-bores;
a middle phalanx having a flat distal end, a curved proximal end, and a pair of radially spaced-apart, longitudinally oriented through-bores; and
a distal phalanx having a distal end, a curved proximal end, and a pair of radially spaced-apart, longitudinally oriented through-bores wherein said at least one link member extends through each of said radially spaced-apart, longitudinally oriented through-bores.

29. A surgical probe according to claim 28 wherein said curved proximal end of said distal phalanx is pivotally connected to said flat distal end of said middle phalanx and said curved distal end of said elongate proximal phalanx is pivotally connected to said curved proximal end of said middle phalanx so as to comprise a range of motion when a portion of said at least one link member is placed in tension, that is continuous between a first fully extended position that is aligned with said longitudinal axis and a substantially crook position.

30. A surgical probe according to claim 29 wherein a range of motion of said articulated digit is limited by an interactive, rolling engagement of (i) said curved proximal end of said distal phalanx with said flat distal end of said middle phalanx and, (ii) said curved distal end of said elongate proximal phalanx with said curved proximal end of said middle phalanx.

31. A surgical probe according to claim 29 wherein said first fully extended position locates a dorsal portion of said curved proximal end of said distal phalanx in blocking relation with said dorsal portion of said flat distal end of said middle phalanx so as to prevent further pivotal rotation, and a dorsal portion of said curved distal end of said elongate proximal phalanx is blocked from further rolling engagement by a dorsal portion of said curved proximal end of said middle phalanx.

32. A surgical probe according to claim 29 wherein said substantially crook position locates (i) an anterior portion of said curved proximal end of said distal phalanx in blocking relation with an anterior portion of said flat distal end of said middle phalanx and, (ii) an anterior portion of said curved distal end of said elongate proximal phalanx in blocking relation with an anterior portion of said curved proximal end of said middle phalanx.

33. A surgical probe allowing a surgeon to manipulate tissue while maintaining a kinesthetic relationship between the surgeon's finger during a surgical procedure, said probe, said probe comprising:
an elongated member extending from a first section of a body portion, said first section being in alignment with said elongated member;
a segmented digit located at a far end of said elongated member, said segmented digit having at least a tip portion and a middle portion where said tip and middle portion are pivotally connected such that said tip portion and middle portion may move between a straight profile and a curved profile, where in said curved profile said segmented digit curves in a manner similar to the surgeon's finger;
an operating actuator pivotally moveable between a proximal and distal positions and extending from first section of said body portion such that said operating actuator is limited to pivot in longitudinal alignment with both said segmented digit and said first section of said body portion, where said operating actuator is coupled to said segmented digit by at least one link member where a proximal end of said link member is affixed to said actuator, where said link member provides direct force feedback to said operating actuator from said articulated digit as said operating actuator moves between said distal and proximal positions to move said segmented digit between said straight profile and curved profile; and where proximal movement of said operating actuator by the surgeon's finger to said proximal position causes said link member to be placed in tension such that the surgeon maintains the kinesthetic relationship via said actuator from the link member in tension.

34. The surgical probe of claim 33, where the segmented digit further includes a rear portion pivotally connected to the middle portion at an opposite end of the tip portion.

35. The surgical probe of claim 33, wherein said segmented digit includes a gauze pad fastened to a tip.

36. The surgical probe of claim 33, wherein said link member comprises a wire.

37. The surgical probe of claim 33, wherein a surgeon's perception of a motion, weight, and position of said segmented digit, relative to a tissue being probed, is maintained as the muscles, tendons, and joints of said surgeon's finger move said operating actuator causing said segmented digit to move between a continuous range of positions.

38. A surgical probe according to claim 33, wherein a spring and damper sensation is transferred by said link member to the surgeon when actuating said segmented digit so as to engage a tissue structure.

39. A surgical probe according to claim 33, comprising a tip that projects outwardly from a distal end of said segmented digit so as to provide a tactile pad for use in manipulating or dissecting tissue during surgery.

40. A surgical probe according to claim 33, wherein said operating actuator includes a plurality of link members arranged in a linkage mechanism operatively connected to said segmented digit.

41. A surgical probe according to claim 33, wherein said operating actuator comprises a locking mechanism allowing one-handed operation.

42. A surgical probe according to claim 33, wherein said articulated digit is sheathed with a polymeric material so as to better approximate the diameter, contour, and shape of a human finger.

43. A surgical probe according to claim 33 wherein said segmented digit comprises a releasable tip.

44. A surgical probe according to claim 33, wherein said bulbous tip includes at least one of a light source and a cautery.

45. A surgical probe according to claim 33, wherein said segmented digit comprises a plurality of shapes and contours of a human finger.

46. The surgical probe of claim 33, where said actuator extends such that the operator's finger engaging said lever moves from a straight profile to a curved profile while being longitudinally aligned with said segmented digit.

* * * * *